(12) United States Patent
Magers et al.

(10) Patent No.: US 10,376,639 B2
(45) Date of Patent: Aug. 13, 2019

(54) VALVING SYSTEM FOR INFUSION CASSETTE

(71) Applicant: CareFusion 2200, Inc., San Diego, CA (US)

(72) Inventors: Corey Michael Magers, Oceanside, CA (US); Edward Browka, Oneida, NY (US)

(73) Assignee: CareFusion 2200, Inc., San Diego, CA (US)

( * ) Notice: Subject to any disclaimer, the term of this patent is extended or adjusted under 35 U.S.C. 154(b) by 706 days.

(21) Appl. No.: 14/749,540

(22) Filed: Jun. 24, 2015

(65) Prior Publication Data

US 2016/0151566 A1 Jun. 2, 2016

Related U.S. Application Data

(63) Continuation-in-part of application No. 14/557,446, filed on Dec. 1, 2014.

(51) Int. Cl.
*A61M 5/168* (2006.01)
*A61M 5/14* (2006.01)
(Continued)

(52) U.S. Cl.
CPC ........ *A61M 5/16813* (2013.01); *A61M 5/145* (2013.01); *A61M 5/1413* (2013.01);
(Continued)

(58) Field of Classification Search
CPC .............. A61M 5/365; A61M 5/14586; A61M 5/1452; A61M 5/142; A61M 5/145;
(Continued)

(56) References Cited

U.S. PATENT DOCUMENTS

| | | |
|---|---|---|
| 4,842,584 A | 6/1989 | Pastrone |
| 5,098,262 A | 3/1992 | Wecker et al. |

(Continued)

FOREIGN PATENT DOCUMENTS

| | | |
|---|---|---|
| WO | WO-2005097235 A2 | 10/2005 |
| WO | WO-2014190188 A2 | 11/2014 |
| WO | WO-2016190904 A1 | 12/2016 |

OTHER PUBLICATIONS

International Search Report and Written Opinion for Application No. PCT/US2015/063001, dated Mar. 8, 2016, 22 pages.
(Continued)

*Primary Examiner* — Imani N Hayman
*Assistant Examiner* — Tiffany Legette
(74) *Attorney, Agent, or Firm* — Morgan, Lewis & Bockius LLP

(57) ABSTRACT

Pump cassettes, infusion systems, and methods are described. An example infusion pump system may include a cassette recess with one or more valve actuators that extend through a surface of the cassette recess to operate a corresponding valve in a fluid passageway of a pump cassette mounted in the cassette recess. The valve actuator may include a base portion, a shaft extending from the base portion through the surface, and a spring disposed on the shaft and extending along a portion of the shaft. The spring may be disposed interior to the back surface. The system may include first and second valve actuators configured to operate corresponding first and second valves located on opposing sides of a pump chamber of the fluid passageway. A piston may be configured to cooperate with the first and second valve actuators to pump a fluid through the fluid passageway.

19 Claims, 27 Drawing Sheets

(51) Int. Cl.
*A61M 5/145* (2006.01)
*A61M 39/22* (2006.01)
*A61M 5/142* (2006.01)

(52) U.S. Cl.
CPC ............. *A61M 2005/14208* (2013.01); *A61M 2005/14288* (2013.01); *A61M 2039/226* (2013.01)

(58) Field of Classification Search
CPC .... A61M 5/16813; A61M 2005/14208; A61M 2005/14288; A61M 2039/226; A61M 5/1413; A61M 5/14208; A61M 5/14288; F04B 43/12
See application file for complete search history.

(56) References Cited

U.S. PATENT DOCUMENTS

| | | | |
|---|---|---|---|
| 5,554,013 A * | 9/1996 | Owens | A61M 5/14224 417/413.1 |
| 5,575,632 A | 11/1996 | Morris et al. | |
| 5,807,075 A | 9/1998 | Jacobsen et al. | |
| 5,816,779 A | 10/1998 | Lawless et al. | |
| 5,954,485 A | 9/1999 | Johnson et al. | |
| 6,475,178 B1 | 11/2002 | Krajewski et al. | |
| 7,867,189 B2 | 1/2011 | Childers et al. | |
| 7,972,306 B2 | 7/2011 | Shearn | |
| 8,066,671 B2 | 11/2011 | Busby et al. | |
| 8,465,454 B2 | 6/2013 | Kirkpatrick | |
| 8,523,816 B2 | 9/2013 | Kirkpatrick | |
| 8,668,671 B2 | 3/2014 | Kirkpatrick | |
| 8,771,228 B2 | 7/2014 | Butterfield | |
| 8,784,359 B2 | 7/2014 | Plahey et al. | |
| 8,936,447 B2 | 1/2015 | Abal | |
| 2001/0051789 A1 | 12/2001 | Parsons | |
| 2004/0019313 A1 | 1/2004 | Childers et al. | |
| 2007/0213653 A1 * | 9/2007 | Childers | A61M 1/1696 604/29 |
| 2008/0138223 A1 | 6/2008 | Lanigan et al. | |
| 2008/0262409 A1 | 10/2008 | Derrico et al. | |
| 2009/0062738 A1 | 3/2009 | Ziegler | |
| 2010/0286599 A1 | 11/2010 | Ziegler et al. | |
| 2011/0040244 A1 * | 2/2011 | Busby | A61M 1/28 604/29 |
| 2011/0178359 A1 | 7/2011 | Hirschman et al. | |
| 2011/0282276 A1 | 11/2011 | Abal | |
| 2012/0053557 A1 | 3/2012 | Abal | |
| 2012/0078218 A1 | 3/2012 | Barnes | |
| 2012/0083759 A1 | 4/2012 | Kirkpatrick | |
| 2012/0177543 A1 | 7/2012 | Battrell et al. | |
| 2012/0179130 A1 | 7/2012 | Barnes et al. | |
| 2013/0106609 A1 | 5/2013 | Singh et al. | |
| 2013/0267899 A1 | 10/2013 | Robert et al. | |
| 2014/0276424 A1 | 9/2014 | Davis et al. | |
| 2014/0276426 A1 | 9/2014 | Borges et al. | |
| 2014/0276533 A1 | 9/2014 | Butterfield et al. | |
| 2016/0151561 A1 | 6/2016 | Toro et al. | |
| 2017/0032152 A1 | 2/2017 | Salem et al. | |

OTHER PUBLICATIONS

International Search Report and Written Opinion for Application No. PCT/US2015/063002, dated Mar. 8, 2016, 11 pages.
International Search Report and Written Opinion for Application No. PCT/US2015/063007, dated Mar. 8, 2016, 10 pages.
International Search Report and Written Opinion for Application No. PCT/US2015/063010, dated Mar. 8, 2016, 13 pages.
International Search Report and Written Opinion for Application No. PCT/US2015/063013, dated Mar. 8, 2016, 15 pages.
Extended European Search Report for Application No. 15864547.3, dated Aug. 1, 2018, 7 pages.
Extended European Search Report for Application No. 15865327.9, dated Aug. 1, 2018, 7 pages.

* cited by examiner

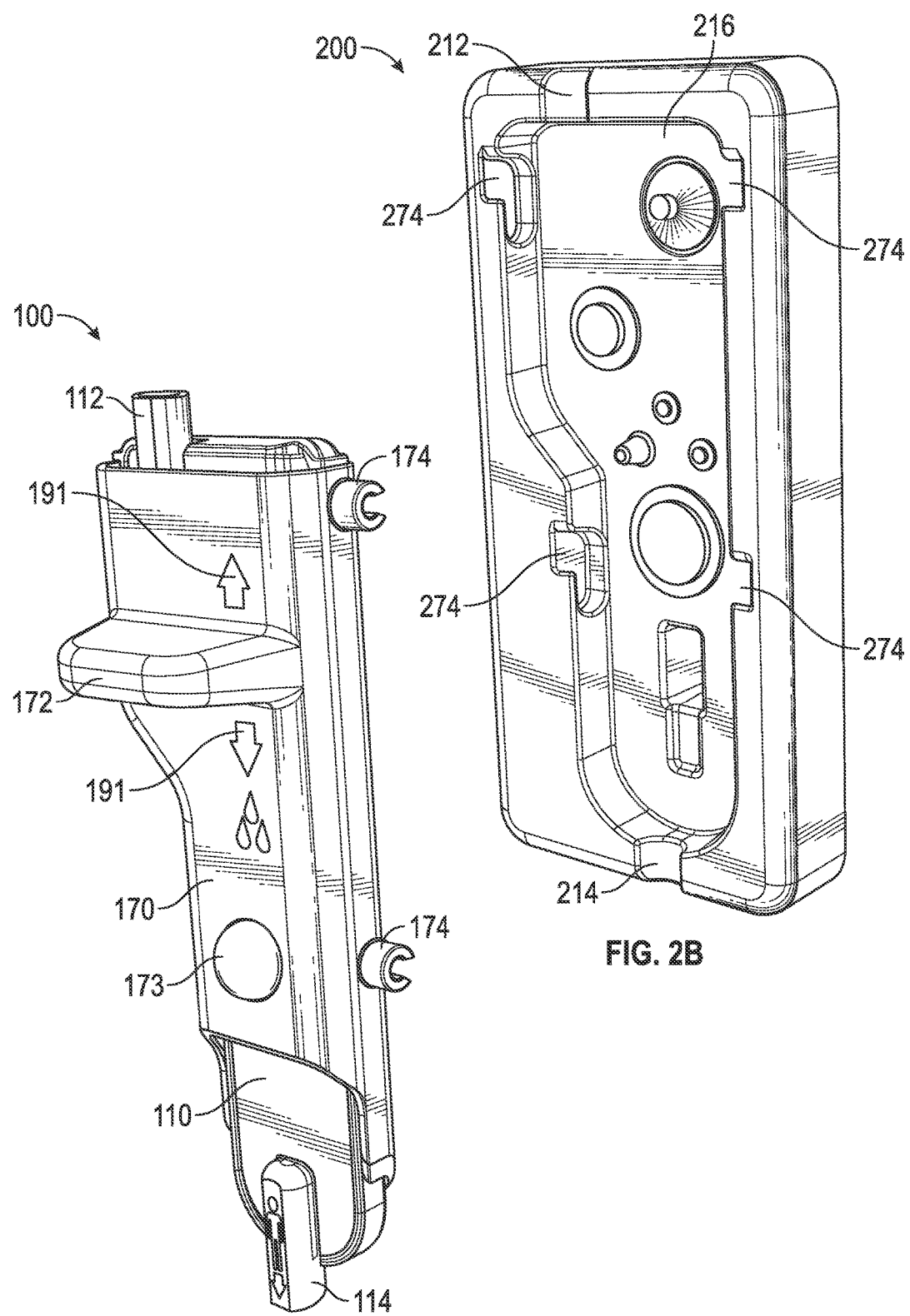

VALVING SYSTEM FOR INFUSION CASSETTE

CROSS-REFERENCE TO RELATED APPLICATION

This application is a continuation-in part of U.S. patent application Ser. No. 14/557,446, titled "PUMP CASSETTES WITH SLIDER AND INFUSION PUMP SYSTEMS," filed on Dec. 1, 2014, the entire contents of which are hereby incorporated by reference herein for all purposes.

TECHNICAL FIELD

The present disclosure generally relates to apparatus, systems, and methods of delivering medical fluid to patients, and more particularly to infusion pumps, disposable cassettes, and associated methods.

BACKGROUND

Infusion pumps are medical devices that may be used to administer intravenous (IV) fluids. An infusion pump can facilitate the delivery of IV fluids while controlling the volumes and rates for the delivery of such IV fluids. The IV fluids may be delivered at continuous rates or intermittent intervals. Some infusion pumps move fluid through an IV tube using a peristaltic pumping mechanism that acts on the IV tube, while other infusion pumps rely on a cartridge or cassette-like device intended to be manipulated by a pump to cause the IV fluid to flow at the controlled rate or interval. In either case, a typical infusion pump, manipulates the IV tube or IV cartridge such that the IV fluid moves from a container to a patient. The IV tube or IV cartridge is typically connected to or integrated with an IV set (e.g., tubing, valves, and fittings for delivering fluid to a patient), and therefore the cartridge and IV set may be disposable to reduce the risk of infection and contamination.

SUMMARY

Aspects of the subject technology relate to disposable IV pump cassettes and infusion pump systems. A pump cassette may have a controllable fluid passageway formed in part by a compliant membrane. One or more valves in the fluid passageway may be operated by compressing portions of the compliant membrane with one or more valve actuator members to seal portions of the passageway. One or more valve actuators may be disposed in a cassette recess for receiving the pump cassette such that each of the valve actuators protrude through a back surface of the cassette recess to operate a corresponding valve in a fluid passageway. A valve actuator may include a base portion, a shaft extending from the base portion through the surface, and a spring disposed on the shaft and extending along a portion of the shaft. The spring may be disposed interior to the back surface. In accordance with some embodiments, the one or more valves may include an inlet-side valve on a first side of a pump chamber in the fluid passageway and an outlet-side valve on an opposing side of the pump chamber. A piston may be configured to cooperate in coordinated movement with valve actuators associated with the inlet-side and outlet-side valves to pump a fluid through the fluid passageway.

In accordance with certain aspects, an infusion pump system may be provided that includes a processing unit and a cassette recess including at least one valve actuator configured to extend through a surface of the cassette recess to operate a valve in a fluid passageway of a cassette mounted in the cassette recess, where the at least one valve actuator includes: a base portion; a shaft extending from the base portion through the surface; and a spring disposed on the shaft and extending along a portion of the shaft, wherein the spring is disposed interior to the surface.

In accordance with certain aspects, a valve actuator may be provided that includes: a base portion; a shaft extending from the base portion; a spring disposed on the shaft and extending along a portion of the shaft; and a rotatable member disposed on the base portion and configured to be engaged by a cam structure for actuating the valve actuator in a direction substantially parallel to the shaft.

In accordance with certain aspects, a method of operating an infusion pump system may be provided, the method including: providing a pump cassette in a cassette recess of the infusion pump system; and operating a valve of a controllable fluid passageway in the pump cassette by actuating a valve actuator that extends through a back surface of the cassette recess to contact a membrane of the pump cassette, where the valve actuator includes: a base portion; a shaft extending from the base portion through the back surface; and a spring disposed on the shaft and extending along a portion of the shaft, wherein the spring is disposed interior to the back surface.

It is understood that in accordance with certain aspects, the cassette recess may be integrated into the same box as a processing unit or may be contained in an interface module that may be operatively coupled to a processing unit.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 2A and 2B illustrate perspective views of examples of a first embodiment disposable IV pump cassette and cassette recess, in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1A:
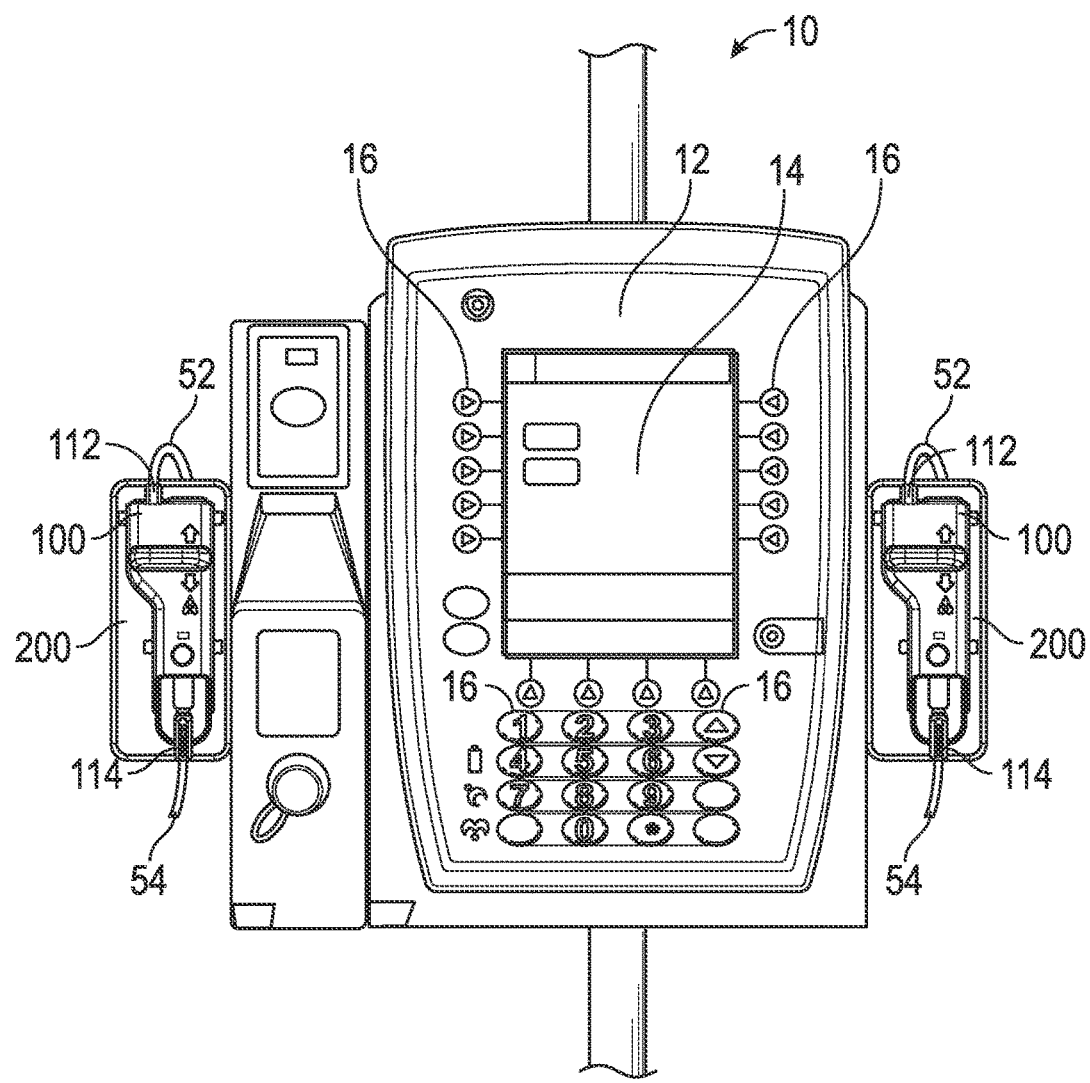
FIGS. 1A and 1B are overview diagrams illustrating examples of infusion pump systems, in accordance with aspects of the present disclosure.

FIG. 1A illustrates an example of an infusion pump system. In accordance with certain embodiments, infusion pump system 10 may include one or more cassette recesses and disposable IV pump cassettes (e.g., cassette recesses 200, 400, 800, 1000 and cassettes 100, 300, 700, 900). For example, cassette recess 200 may be configured to receive cassette 100 and provide various mechanical couplings and operational interfaces (e.g., fittings, motor, gearing, driveshaft, sensors, etc.). Infusion pump system 10 may include central processing unit 12 with display screen 14 (e.g., touchscreen display), and a data input features 16, for example, a keypad and a series of configurable buttons adjacent to display screen 14. Other types of input and output devices may be used with central processing unit 12 and infusion pump system 10. In certain aspects, central processing unit 12 is operatively coupled to one or more interface modules, with cassette recesses 200, to control and communicate with various operational interfaces thereof.

Figure 1B:
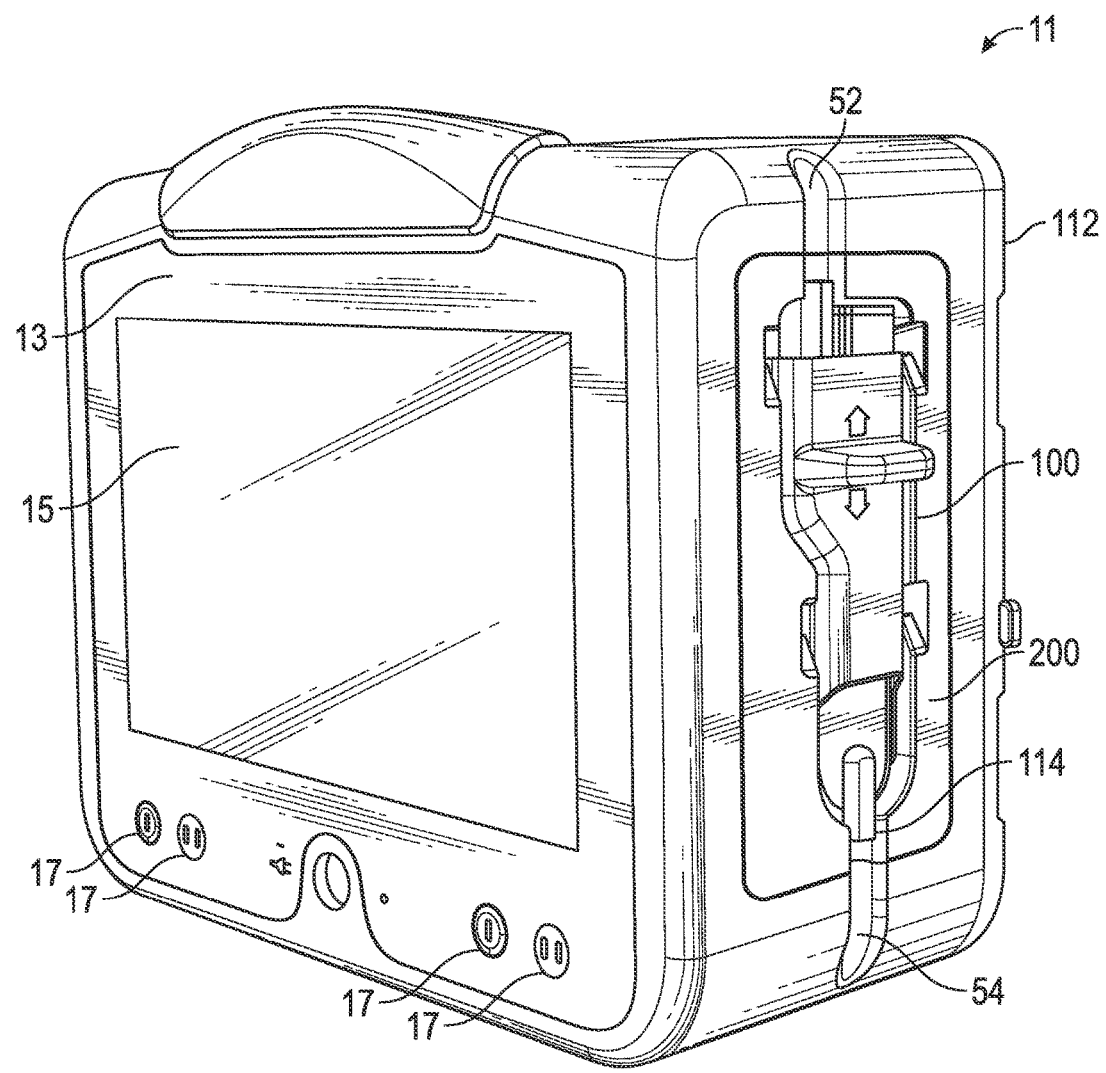

FIG. 1B illustrates another example of an infusion pump system. In accordance with certain embodiments, infusion pump system 11 may include one or more cassette recesses and disposable IV pump cassettes (e.g., cassette recesses 200, 400, 800, 1000 and cassettes 100, 300, 700, 900). For example, cassette recess 200 may be configured to receive cassette 100 and provide various mechanical couplings and operational interfaces (e.g., fittings, motor, gearing, driveshaft, sensors, etc.). Infusion pump system 11 may include central processing unit 13 with display screen 15 (e.g., touchscreen display), and a data input features 17, for example, a series of configurable buttons adjacent to display screen 15. In some implementations, the display screen 15 may provide a keypad or similar data entry feature. Other types of input and output devices may be used with central processing unit 13 and infusion pump system 11. In certain aspects, central processing unit 13 is operatively coupled to one or more interface modules, with cassette recesses 200, to control and communicate with various operational interfaces thereof.

In operation, an IV bag, syringe or other fluid source 52 may be fluidly connected to inlet 112 of cassette 100, and outlet 114 of cassette 100 may be fluidly connected to a patient 54 as shown in the examples of FIGS. 1A and 1B. Infusion pump systems 10 and 11 may be configured to operate over a wide range of infusion rates such as, but not limited to, 1-999 ml/h for general purpose and operating room applications, and 0.1-99.9 ml/h for neonatal applications. Infusion pump systems 10 and 11 may include, for example, low-sorbing configurations compatible with chemotherapy, TPN and Nitroglycerin (NTG). In accordance with some embodiments, cassettes 100 may comprise a DEHP-free and Latex fluid pathway suitable for various patient populations (e.g., neonate, pediatric, and adult).

In accordance with aspects of the subject technology, disposable IV cassettes 100 used with infusion pump systems 10 and 11 may be substantially reduced in size when compared to conventional disposable IV cassette units resulting in a significant amount of medical plastic required to be treated and disposed of in compliance with various regulations.

Additionally, infusion pump systems 10 and 11 comprising externally mounted and translucent cassettes 100 for which fluid passage through the entire fluid pathway, or a portion thereof, in the IV set may be advantageous.

In operation, a user (e.g., a caregiver) may obtain a new disposable IV cassette 100 and prime cassette 100 before inserting cassette 100 into cassette recess 200. Caregiver may check for any visible air bubbles in the fluid pathway and may press on any accessible fluid reservoirs (e.g., pressure dome chambers) to move fluid through the cassette 100. In accordance with certain aspects, cassette 100 can be securely held and inserted into cassette recess 200 by a single hand of a caregiver. In this regard, caregiver's other hand can be freed to perform other tasks.

FIGS. 2A and 2B illustrate examples of a disposable IV pump cassette 100 and corresponding cassette recess 200 of an interface module. In accordance with certain embodiments, cassette 100 may comprise a cassette body 110 and a slider 170. Cassette 100 may include certain may include certain visual indicators related to operation aspects of the cassette and the infusion pump system in general. For example, cassette may include identifiable images such as fluid drops indicating position of slider 170 for free-flow (flow stop valve 164 in an open position) and a patient figure proximal to outlet 114. In accordance with some aspects, cassette 100 may include lens area 173 for magnification of the fluid pathway within the cassette body 110. Lens area 173 may be disposed on the slider 170 or proximal to outlet 114 and/or an air-in-line detection feature. For example, during priming or prepping a cassette, a user or caregiver may use lens area 173 to ensure that any visible air bubbles have been removed and fluid is flowing properly. In accordance with some aspects, one or more cassette-seated sensors may be disposed within the cassette recess 200 so as to inform central processing unit 12 that the cassette is locked or secured into place within the cassette recess 200 or seat.

Slider 170 can be fixably and slidably engaged with cassette body 110 such that slider 170 may articulate longitudinally 191 with respect to cassette body 110, but will be constrained within range of sliding motion such that the slider remains coupled to the cassette body 110. Slider 170 may be formed from rigid plastic or polymer material having lubricating characteristics (e.g., incorporating silicon or polytetrafluoroethylene (PTFE) additives), and is clear or translucent in accordance with certain embodiments. In some embodiments, slider 170 may be polycarbonate. Slider 170 includes a slider grip 172 or handle portion and a plurality of protrusions 174 or lugs that are configured to be releasably lockable with a plurality of slots 274 of the cassette recess 200 (e.g., L-shaped locking channels). The plurality of protrusions 174 may be disposed at various locations on slider 170. In this regard, cassette 100 can be self-latched into the cassette recess 200. Accordingly, a door or lever action is not required in order to retain the cassette 100 within the cassette recess 200. In an alternative embodiment, an inverse configuration may be desired, in which the cassette recess 200 would contain protrusions or lugs that would be configured to be releasably lockable with a corresponding slots located on the slider or rigid body.

In operation, cassette 100 can be loaded directly into cassette recess 200. In this regard, the direct loading of the cassette 100 will enable avoidance of sheer forces that might otherwise be applied to the sensors, alignment features, and other engaging interfaces of cassette-facing surface 216 of cassette recess 200 from interaction with the interface-facing side of cassette body 110 as it is loaded into cassette recess 200. Cassette recess 200 may include non-vertically aligned inlet recess 212 and outlet recess 214.

It is to be understood that modification to the various features of cassette 100 can be made to accommodate the various cassette-coupling techniques disclosed herein.

Figure 3A:
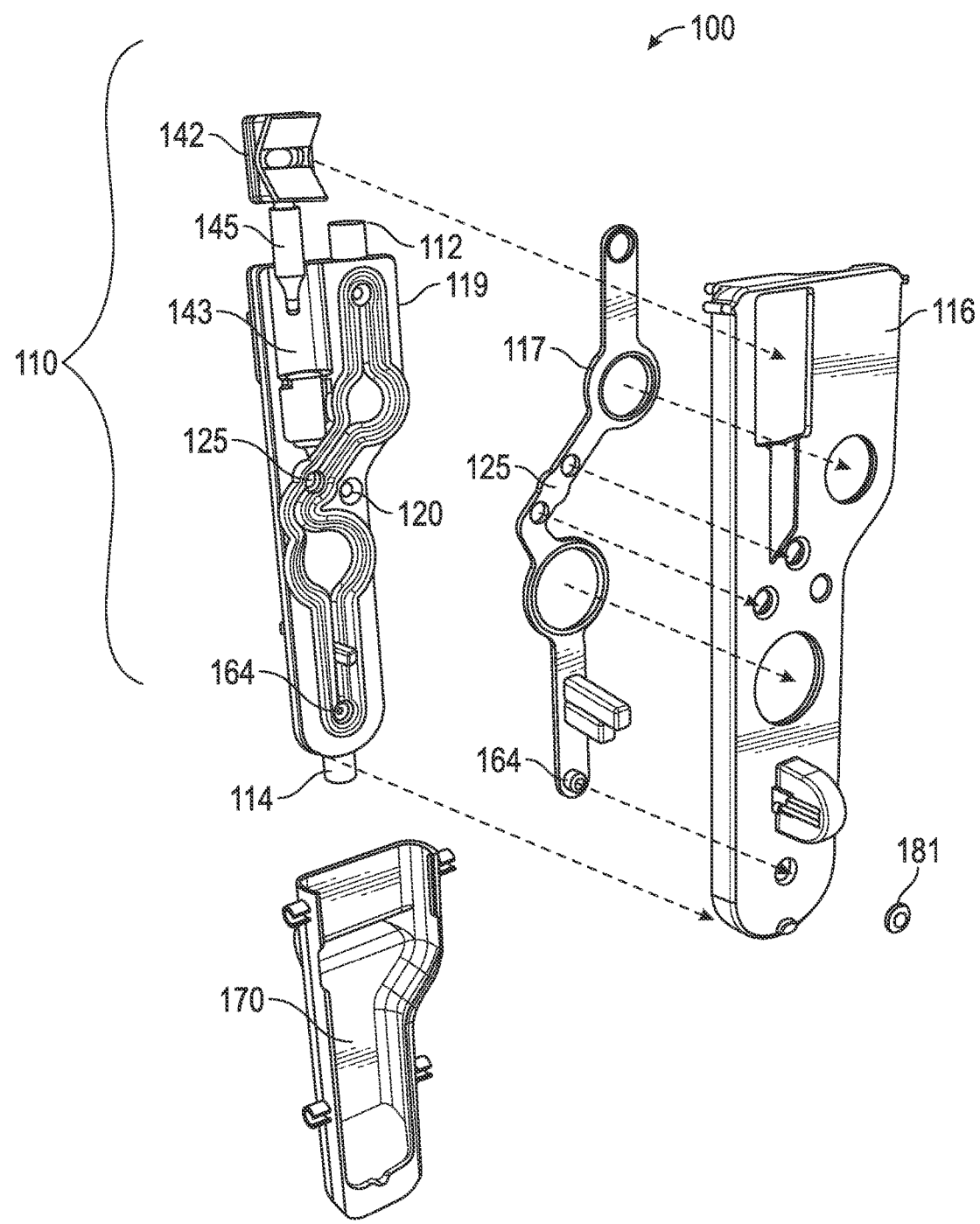
FIG. 3A is an exploded perspective detail view illustrating an example of a first embodiment disposable IV pump cassette, in accordance with aspects of the present disclosure.
Figure 3B:
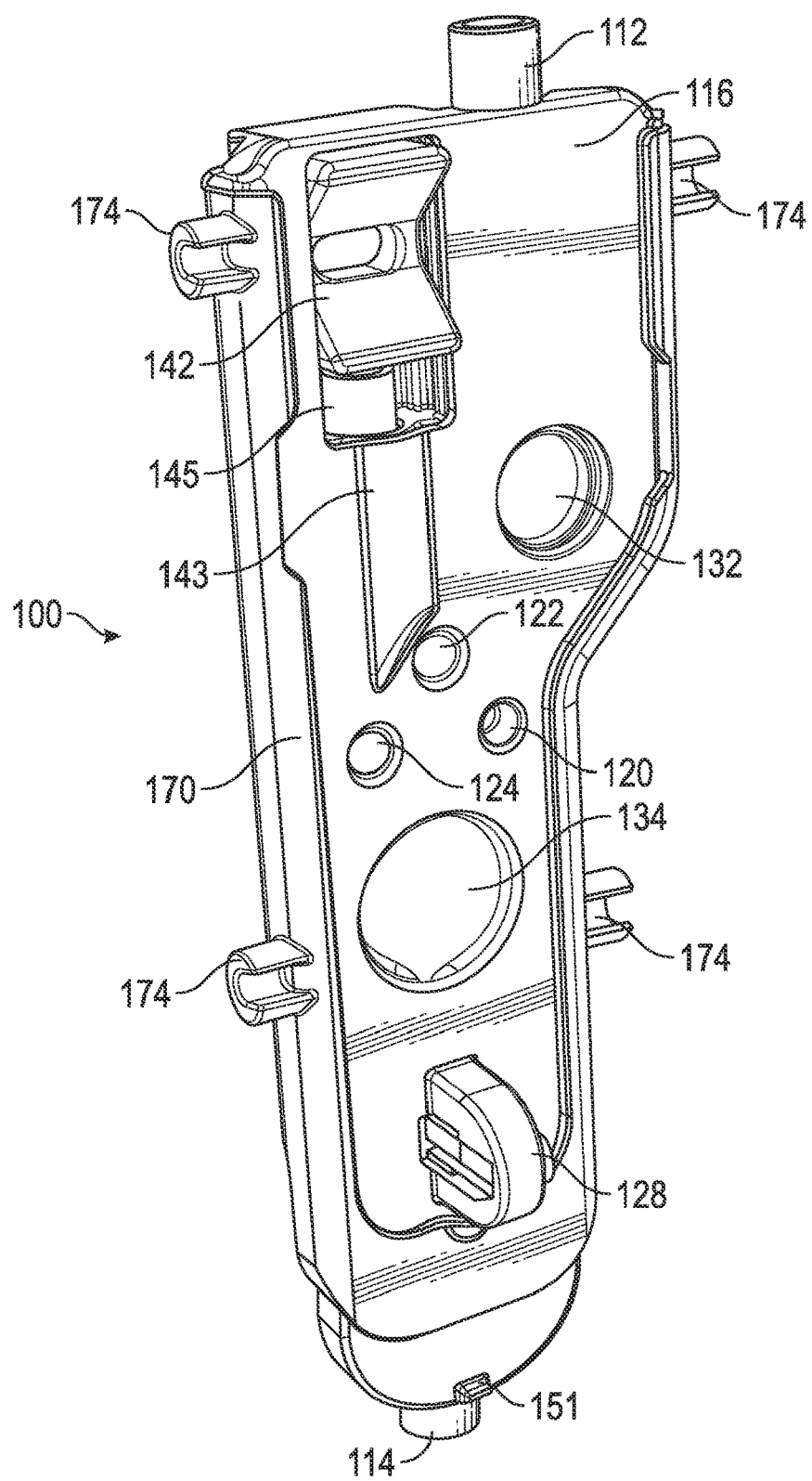
FIG. 3B illustrates a perspective view of an example of a first embodiment disposable IV pump cassette, in accordance with aspects of the present disclosure.

Referring now to the examples of FIGS. 3A and 3B, cassette body 110 may comprise interface-facing frame portion 116 and slider-facing base portion 119 with membrane 117 disposed substantially therebetween (e.g., portions of membrane 117 may extend through some openings of frame portion 116). In accordance with certain embodiments, membrane 117 can be a compliant material co-molded to the frame portion 116 and sealingly engaged with base portion 119 for defining a fluid pathway through cassette body 110 from inlet 112 to outlet 114. Mating edges of frame portion 116 and base portion 119 may be connected by fusing, welding, gluing, or the like. Membrane 117 and base portion 119 may further define a plurality of other features, some of which may be accessed through openings in frame portion 116.

Frame portion 116, membrane 117, and/or base portion 119 may define features in or along the fluid pathway, in accordance with certain embodiments. For example, beginning from inlet 112, the fluid pathway may include features such as, but not limited to, upstream pressure dome 132 (e.g., an inlet-side compliant reservoir), inlet-side valve 122, pump chamber having pump chamber opening/access 125, outlet-side valve 124, downstream pressure dome 134 (e.g., an outlet-side compliant reservoir), fluid pathway extension member 128, and flow stop valve 164. Other features that are not in or along the fluid pathway, but are disposed on cassette body 110, may include positioning port 120 and slider stopper 151. With respect to extension member 128, a portion of the fluid pathway can be extended away or protrude orthogonally from the generally flat and planar exterior surface of interface-facing frame portion 116 so as to make the fluid in the fluid pathway available for certain detection techniques performed by infusion pump system 10, 11. As illustrated in the example of FIGS. 3A and 3B, fluid pathway extension member 128 may be formed from orthogonally extending portions of frame portion 116, membrane 117, and/or base portion 119.

In accordance with certain embodiments, membrane 117 may be formed from a thermoplastic elastomer (TPE). Characteristics of certain TPEs can enable effective co-molding with other materials, for example, polycarbonate. Accordingly, in some embodiments, membrane 117 may be co-molded to frame portion 116 and striker 181 may be co-molded to a portion of membrane 117 defining a flow stop valve 164. However, in some embodiments, membrane 117 can be formed from silicon, a silicon-based compound, an elastomeric material suitably compliant for fluid flow, or the like.

In accordance with certain embodiments, interface-facing frame portion 116 and slider-facing base portion 119 may be formed from a rigid plastic such as, but not limited, a polycarbonate. Additionally, the rigid plastic of frame portion 116 and base portion 119 may be clear or translucent. The material of membrane 117 (e.g., TPE or other compliant material) and rigid plastic slider 170 may also be clear or translucent, thereby allowing a user or caregiver to readily observe fluid passage through a substantial portion of the fluid pathway of cassette body 110. In some embodiments, the fluid pathway portion of cassette body 110 will be clear or translucent, and other portions will be frosted so as to direct a user or caregiver's attention to the fluid pathway.

In some implementations, slider 170, base portion 119, and membrane 117 may be clear or translucent (or at least some portions along the fluid pathway), and the frame portion 116 may not be translucent. For example, the frame portion 116 may be colored in a manner so as to contrast against a color or tint of the fluid expected to be used with cassette 100. In some embodiments, a lens area 173 may be disposed on base portion 119 alternatively, or in addition to, lens area 173 disposed on slider 170.

Figure 3C:
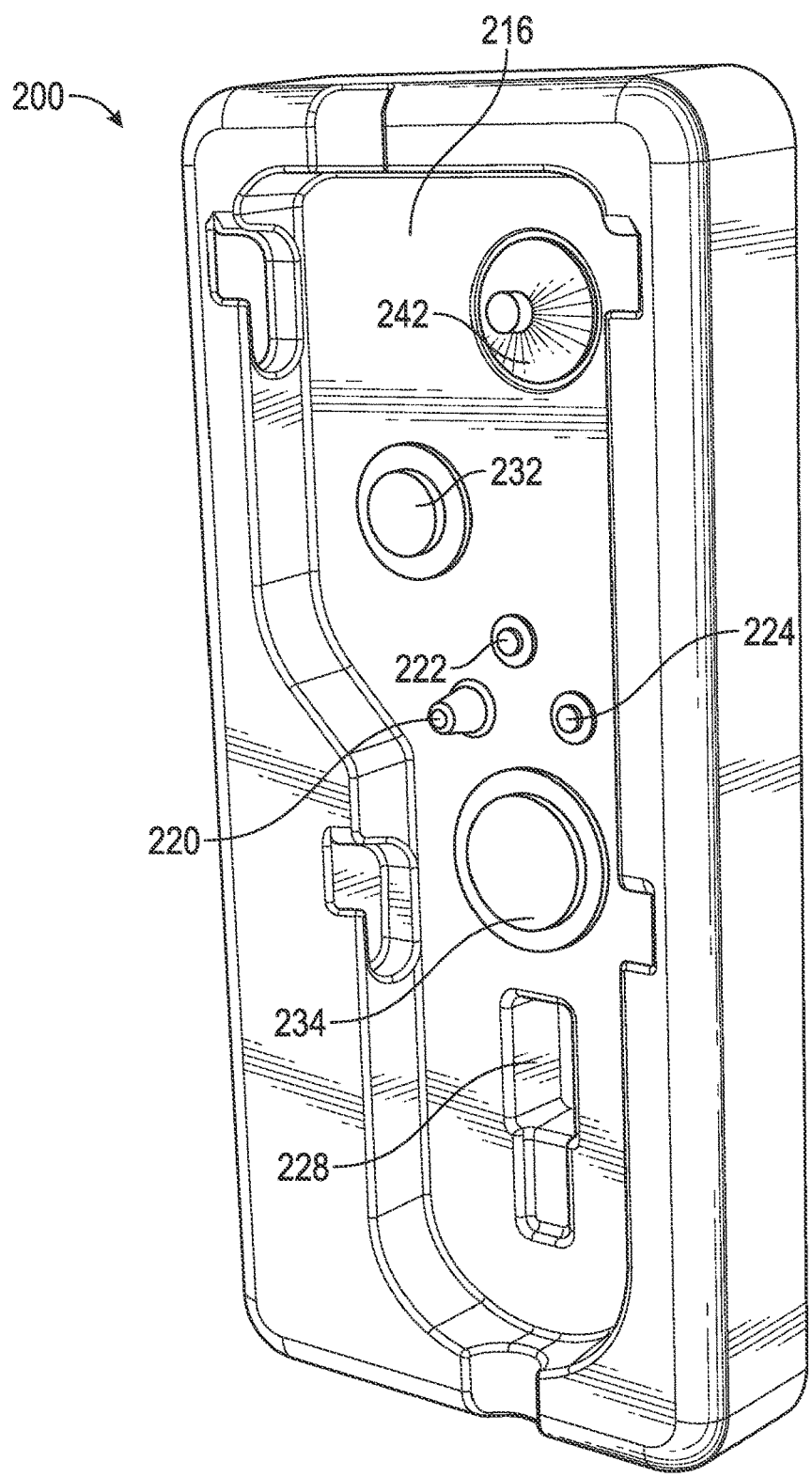
FIG. 3C illustrates a perspective view of an example of a first embodiment cassette recess, in accordance with aspects of the present disclosure.

With additional reference to the example of FIG. 3C, one or more fluid sensors may be disposed within sensor slot 228. The one or more fluid sensors disposed within sensor slot 228 can be ultrasonic sensors configured as an air-in-line detector, for example. In certain embodiments, extension member 128 may be disposed on cassette body 110 and positioned along the fluid pathway between downstream pressure dome 134 and flow stop valve 164. However, in some embodiments, extension member 128 can be positioned at other locations along the fluid pathway such as, but not limited to, between inlet 112 and upstream pressure dome 132. Additionally, in other embodiments, a plurality of extension members 128 with a plurality of corresponding sensor slots 228 may be positioned along a fluid pathway of cassette body 110.

As illustrated in the examples of FIG. 3A-3C, cassette body 110 may include a pump drive assembly in accordance with certain embodiments. For example, the pump drive assembly may include pump drive interface 142 for receiving pump actuator 242 of cassette recess 200. Pump drive interface 142 can be operatively coupled to piston 145 slidably engaged within piston guide 143 or casing (e.g., generally cylindrical or frustoconical casing) such that reciprocal movement of piston 145 moves within pump chamber providing a seal to urge fluid through the fluid pathway of cassette body 110. In this regard, the pump chamber may be defined by a portion of the piston guide 143 or casing distal from the pump drive interface 142 that is adjacent to and fluidly coupled with a tract or section of the fluid pathway between inlet-side valve 122 and outlet-side valve 124. Thus, pump chamber permits movement of the piston guide 143 with the reciprocal motion of the piston 145 such that a volume of the pump chamber may be varied by movement of the piston 145 in accordance with certain embodiments. In accordance with certain aspects, piston 145 resides and moves within a rigid bore and allows a seal that permits fluid to be drawn into the pump chamber via pump chamber opening/access 125 on the fill cycle and expelled on the delivery cycle.

A wiper seal (not shown) may be positioned within or proximal to piston guide 143 and slidably engaged with piston 145 thereby reducing the possibility of any substances (e.g., dirt or dried fluid particles) near the cassette 100 from contacting one or more slidable seals of the piston 145. The one or more slidable seals of the piston 145 may contact an internal wall piston guide 143 to form a movable barrier of the pump chamber. Additionally, piston 145 may include a reduced tip portion for more precise volumetric displacement of fluid into and out of pump chamber through pump chamber opening/access 125.

For example, pumping operation of infusion pump system 10, 11 when cassette 100 is primed and seated in cassette recess 200 may comprise activating outlet-side valve actuator 224 such that outlet-side valve 124 is closed or sealed while activating inlet-side valve actuator 222 such that inlet-side valve 122 is opened. Opening of inlet-side valve 122 may coincide with or occur shortly before the start of a reverse stroke of piston 145 (e.g., a movement of piston 145 away from pump chamber). Accordingly, fluid can flow from upstream pressure dome 132 to pump chamber. Alternatively, or in addition to, outlet-side valve 124 may comprise a one-way valve mechanism that permits flow of fluid under normal conditions in one direction (from a fluid container to a patient). Additionally, in some alternative embodiments, inlet-side valve 122 may also comprise a one-way valve or choke mechanism permitting flow of fluid in primarily one direction (e.g., from a fluid container to a patient) under normal operating conditions. In this configuration, cassette recess 200 may not need to incorporate either outlet-side valve actuator 224 or inlet-side valve actuator 222. Outlet-side valve 124 and inlet-side valve 122 may limit flow of fluid in one direction, but permit flow in an opposite direction in the event fluid pressure overcomes a cracking pressure of the valves.

Continuing with the valve-operated implementation, pumping operation may comprise activating outlet-side valve actuator 224 such that outlet-side valve 124 is open while activating inlet-side valve actuator 222 such that inlet-side valve 122 is closed or sealed. Opening of outlet-side valve 124 may coincide with or occur shortly before a start of a forward stroke of piston 145 (e.g., a movement of piston 145 toward the opening/access 125 of the pump chamber such that the volume of the pump chamber is reduced). Thus, fluid can flow from pump chamber down the fluid pathway to outlet 114.

In certain embodiments, the upstream pressure dome 132 may be smaller than the downstream pressure dome 134 to minimize retained volume. Likewise, the downstream pressure dome 134 may be larger than the upstream pressure dome 132 to improve resolution of fluid pressure thereby allowing for an accurate and precise volume of fluid to be pumped and any upstream or downstream pressures to be accurately measured.

Referring to FIGS. 3A-3C, pump drive interface 142 and pump actuator 242 may be configured as a reciprocating motion mechanism (e.g., a scotch-yoke configuration) in certain implementations. In such implementations, pump drive interface 142 may include opposing ramp portions for guiding a rotatable pin of pump actuator 242 toward an elongate slot of pump drive interface 142. For example, the outer edges of the opposing ramp portions may be arranged a distance that will ensure engagement with the rotatable pin of pump actuator 242. When the rotatable pin contacts one of the ramp portions, the pump drive interface 142 will move to align the elongate slot of pump drive interface 142 with the with the rotatable pin of pump actuator 242. However, it is to be appreciated that other pump drive assemblies are contemplated with cassette 100 and cassette recess 200 in accordance with the present disclosure.

In certain embodiments, cassette recess 200 may include an upstream pressure sensing probe 232 and downstream pressure sensing probe 234 enabling measurement of in-line pressure and fault isolation to a section of the fluid pathway. For example, upstream pressure sensing probe 232 may operably contact upstream pressure dome 132 through a corresponding opening of interface-facing frame portion 116. Similarly, downstream pressure sensing probe 234 may operably contact downstream pressure dome 134 through a corresponding opening of frame portion 116.

Figure 4:
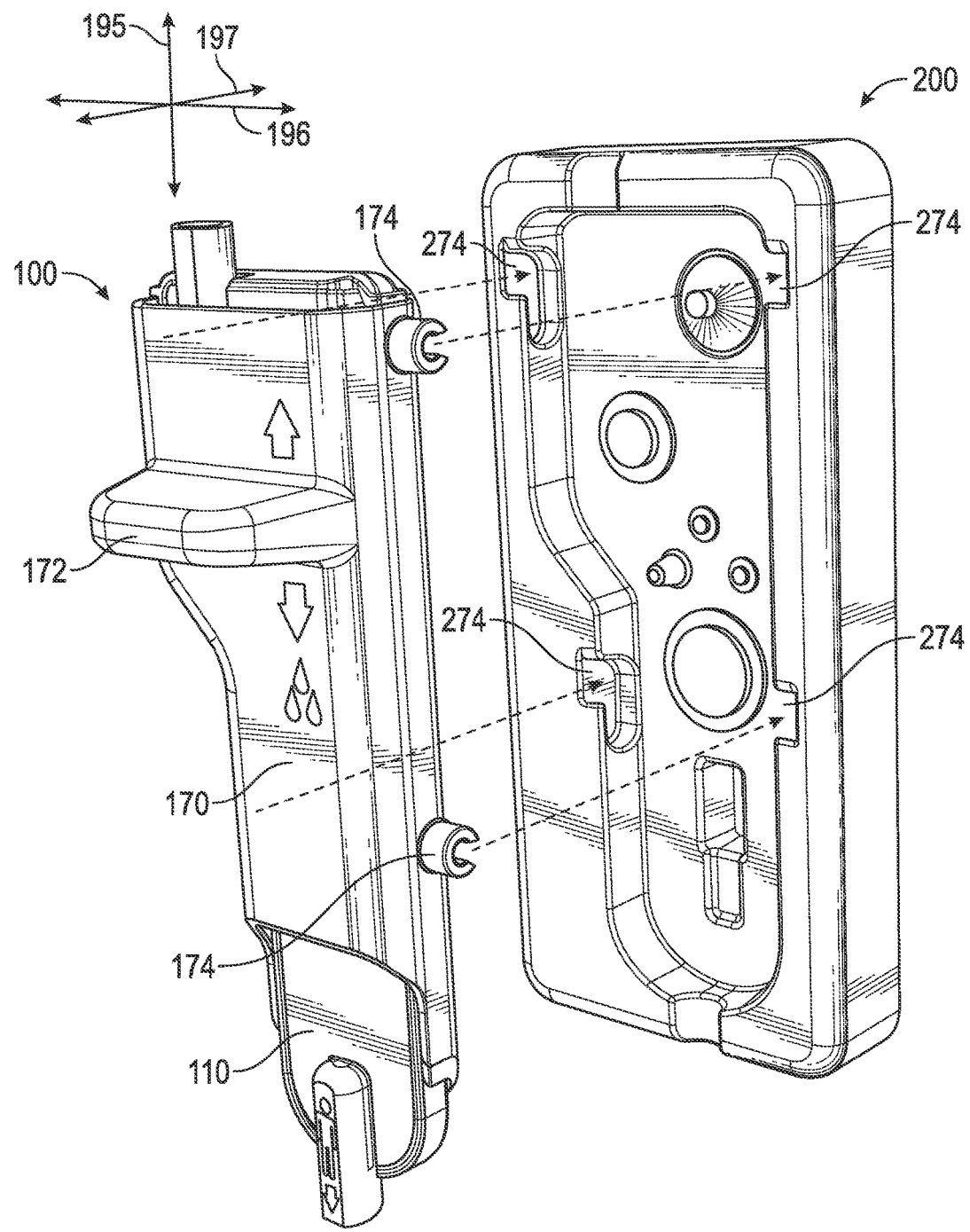
FIG. 4 illustrates perspective views of examples of a first embodiment disposable IV pump cassette and cassette recess, in accordance with aspects of the present disclosure.

FIG. 4 illustrates an example of cassette 100 aligned for insertion with cassette recess 200. Cassette 100 may be aligned such that the plurality of protrusions 174 on slider 170 may be aligned along z-axis 197 for engagement with the plurality of slots 274 of cassette recess 200. In accordance with certain aspects, cassette 100 may have a longitudinal length along y-axis 195, a lateral width along x-axis 196, and a depth along z-axis 197. As illustrated in FIG. 4 and described herein, the depth of the cassette 100 may be a smaller dimension than either the length or the width of cassette 100. In this regard, cassette 100 is front loaded into cassette recess 200.

Figure 5A:
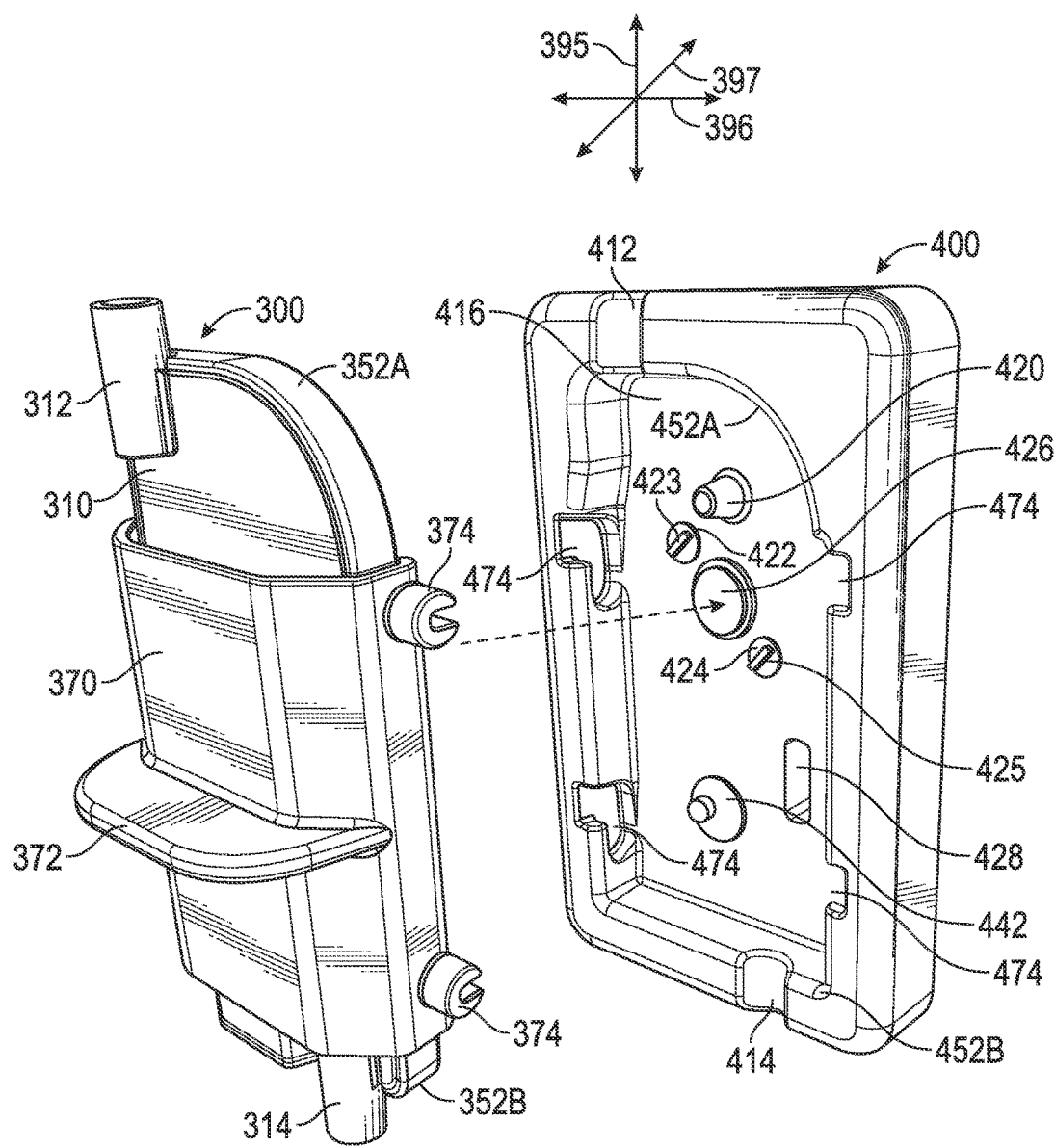
FIG. 5A illustrates perspective views of examples of second embodiment disposable IV pump cassette and cassette recess, in accordance with aspects of the present disclosure.
Figure 5B:
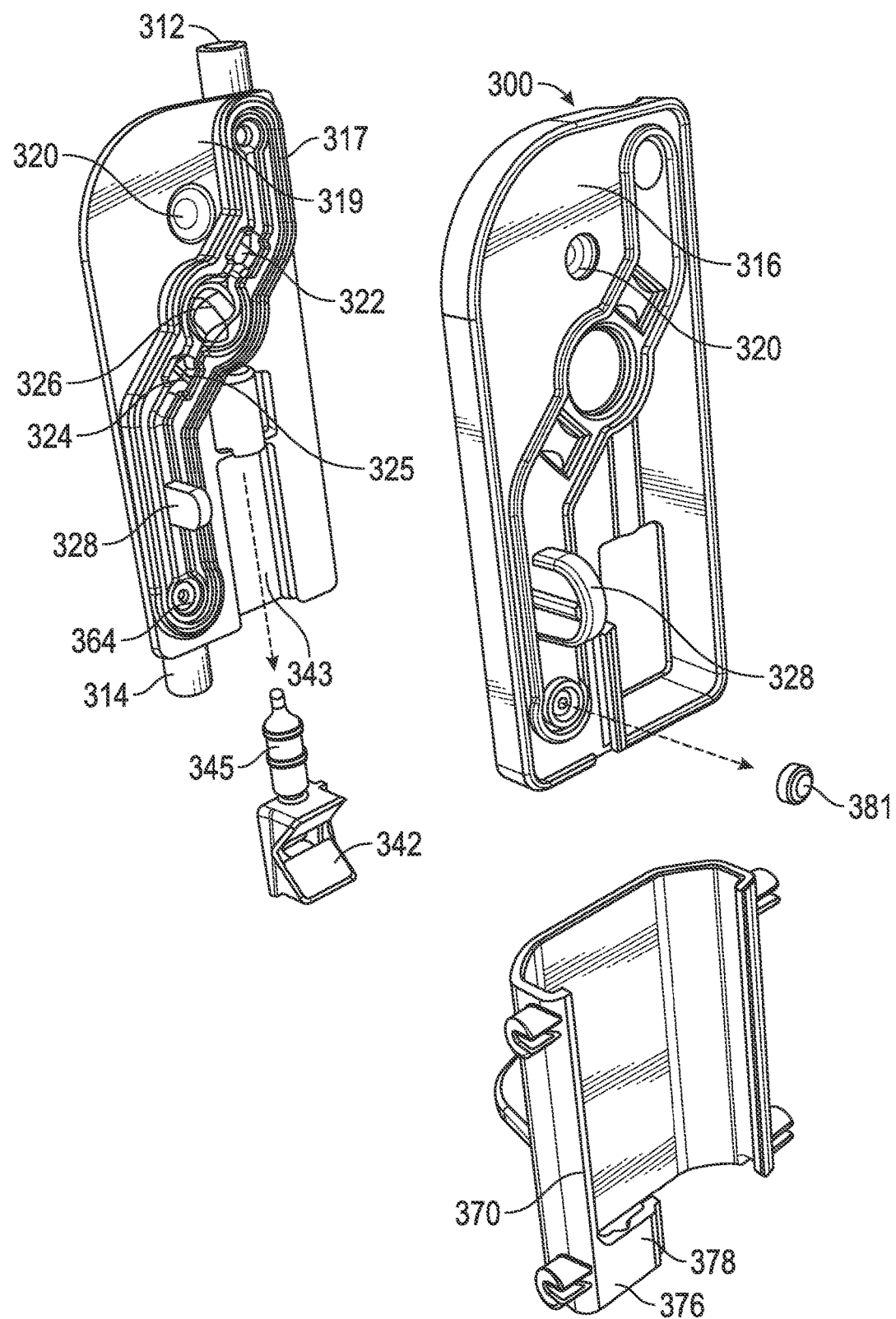
FIG. 5B is an exploded detail view that illustrates a perspective view of second embodiment disposable IV pump cassette, in accordance with aspects of the present disclosure.

FIGS. 5A and 5B illustrate another example of a disposable IV cassette 300 and corresponding cassette recess 400 of an interface module. In accordance with other embodiments, cassette 300 may comprise a cassette body 310 and a slider 370. Cassette 300 may be operatively coupled to cassette recess 400.

In accordance with some embodiments, cassette 300 may comprise a cassette body 310 and a slider 370. Slider 370 can be fixably and slidably engaged with cassette body 310 such that slider 370 may articulate longitudinally with respect to cassette body 310, but will be constrained within range of sliding motion such that the slider remains coupled to the cassette body 310. In some embodiments, cassette 300 may be configured so that slider 370 does not extend around cassette body 310 (FIG. 5B).

In some embodiments, slider 370 includes a slider grip 372 and a plurality of protrusion 374 that are configured to be releasably lockable with a plurality of slots 474 of the cassette recess 400 (e.g., L-shaped locking channels). The plurality of protrusions 374 may be disposed at various locations on slider 370.

Edges 352 of cassette 300 and corresponding perimeter of cassette recess 400 may include at least one arcuate edge 352a contrasted with at least one opposite corner edge 352b, for example. Therefore, orientation of cassette 300 with respect to loading engagement with corresponding arcuate perimeter edge 452a and corner edge 452b of cassette recess 400 may be readily apparent to a user or caregiver.

In accordance with some aspects, an overall size of cassette 300 and cassette recess 400 may be reduced. For example, in some embodiments, cassette body 310 may extended longitudinally a length between 65 mm and 75 mm, for example, by utilizing a single pump chamber/reservoir for sensing probe. Additionally, cassette body 310 may extended laterally a width between 34 mm and 39 mm, and may extend a depth between 10 mm and 14 mm. Fluid pathway extension member 328 may further extend between 8 mm to 10 mm. In some aspects, slider grip 372 may extend between 10 mm to 14 mm from cassette body 310.

For orientation reference with respect to the examples illustrated of FIG. 5A, longitudinal axis or y-axis 395, latitudinal axis or x-axis 396, and depth axis or z-axis 397 are provided. In this regard, depth aspects of cassette 300 is shown in the example of FIG. 5A.

Cassette 300 can be loaded into cassette recess 400. In this regard, the loading of the interface-facing side of cassette body 310 can avoid shear forces applied to the sensors, alignment features, and other engaging interfaces of cassette body and cassette-facing surface 416 of cassette recess 400. The process of cleaning of inlet recess 412, outlet recess 414, and cassette recess 400 is made efficient by the shallow recess configuration in accordance with some embodiments should any fluid or debris accumulate within cassette recess 400.

With reference to the examples of FIG. 5B, cassette body 310 may comprise interface-facing frame portion 316 and slider-facing base portion 319 with membrane 317 disposed substantially therebetween (e.g., portions of membrane 317 may extend through some openings of frame portion 316). In accordance with some embodiments, membrane 317 can be a compliant material co-molded to the base portion 319 and sealingly engaged with frame portion 316 for defining a fluid pathway through cassette body 310 from inlet 312 to outlet 314. In some embodiments, membrane 317 may also be co-molded to striker 381 for defining, in part, a flow stop valve 364.

Mating edges of frame portion 316 and base portion 319 may be connected by fusing, welding, gluing, or the like. Membrane 317 and base portion 319 may further define a plurality of other features, some of which may be accessed through openings in frame portion 319.

Frame portion 316, membrane 317, and/or base portion 319 may define features in or along the fluid pathway, in accordance with some embodiments.

For example, beginning from inlet 312, the fluid pathway may include features such as, but not limited to, inlet-side valve 322, pump chamber/sensing reservoir 326, outlet-side valve 324, fluid pathway extension member 328, and flow stop valve 364. Other features that are not in or along the fluid pathway, but are disposed on cassette body 310, may include positioning port 320. With respect to extension member 328, a portion of the fluid pathway can be extended away or protrude orthogonally from the generally flat and planar exterior surface of interface-facing frame portion 316 so as to make the fluid in the fluid pathway available for other detection techniques performed by infusion pump system 10, 11.

As illustrated, fluid pathway extension member 328 may be formed from orthogonally extending portions of frame portion 316, membrane 317, and base portion 319. However, in other embodiments, a fluid pathway access point may be configured for air-in-line detection, for example, from a section of the exterior surface of interface-facing frame portion 316.

One or more fluid sensors may be disposed within sensor slot 428 such as ultrasonic sensors configured as an air-in-line detector. In some embodiments, extension member 328 may be disposed on cassette body 310 and positioned along the fluid pathway between pump chamber/sensing reservoir 326 and flow stop valve 364.

Cassette body 310 may include a pump drive assembly in accordance with some embodiments. For example, the pump drive assembly may include pump drive mechanism 342 for receiving pump actuator 442 of cassette recess 400. Pump drive mechanism 342 can be operatively coupled to piston 345 slidably engaged within piston guide 343 casing (e.g., generally cylindrical or frustoconical casing) such that reciprocal movement of piston 345 may change a total volume of pump chamber pump chamber/sensing reservoir 326 thereby urging fluid through the fluid pathway of cassette body 310.

In some embodiments, pump drive assembly may be configured to produce a 3.5 mm piston stroke for operation with pump chamber/sensing reservoir 326 configured to be a 10 mm outer diameter reservoir. Moreover, pump drive assembly may be arranged below pump chamber/sensing reservoir 326, in accordance with some embodiments.

With cassette 300 primed and secured in cassette recess 400, an example pumping operation may comprise activating outlet-side valve actuator 424 such that outlet-side valve 324 is closed or sealed while activating inlet-side valve actuator 422 such that inlet-side valve 322 is opened. Opening of inlet-side valve 322 may coincide with or occur shortly after a reverse stroke of piston 345 (e.g., a movement of piston 345 away from pump chamber/sensing reservoir 326). Accordingly, fluid can flow from inlet 312 to pump chamber/sensing reservoir 326. Positioning protrusion 420 may be located proximal to inlet-side valve actuator 422 and aligned above pump chamber sensing probe 426.

Pumping operation may further comprise activating outlet-side valve actuator 424 such that outlet-side valve 324 is open while activating inlet-side valve actuator 422 such that inlet-side valve 322 is closed or sealed. Opening of outlet-side valve 324 may coincide with or occur shortly before a forward stroke of piston 345 (e.g., a movement of piston 345 toward pump chamber/sensing reservoir 326 such that contact is by a head of piston 345 is made with a portion of pump chamber/sensing reservoir 326). Thus, fluid can flow from pump chamber/sensing reservoir 326 to outlet 314.

Therefore, fluid leakage can be avoided during the final preparation stages (e.g., after priming of cassette 300) and prior to insertion into cassette recess 400. During insertion of cassette 300, once cassette body 310 is placed in cassette recess 400, slider 370 can be slid to a second position with respect to cassette body 310 (e.g., articulated downwardly in some implementations). In some embodiments, cassette recess 400 may include pump chamber sensing probe 426 to enable measurement of in-line pressure. When the slider 370 is positioned in the first position, the portion of interface-facing slider section 376 contacts and activates flow stop valve 364 such that fluid flow is occluded at that position of the fluid pathway proximal to outlet 314 cassette body 310. In the second position, flow stop valve 364 may be aligned under a stop valve guard 378 (e.g., ramped or recessed surface) of interface-facing slider section 376 of slider 370.

As shown in FIG. 5A, in some embodiments, valve actuators may be provided with one or more features such as protrusion 423 on inlet-side valve actuator 422 and protrusion 425 on inlet-side valve actuator 424 may be provided for enhancing the seal formed by the valve actuators and membrane 317 when the valve actuators press membrane 317 against cassette body 310 to respectively close valves 322 and 324. As shown in FIG. 5B, corresponding features such as a recess 325 (corresponding to the protruding rib 425 on outlet-side valve actuator 424) may be provided on cassette body 310 that receive and engage with the corresponding features on the valve actuator. Although not visible in FIG. 5B, a similar recess for receiving protrusion 423 of inlet-side valve actuator 422 may be provided in cassette body 310 in valve 322. Features such as protrusions 423 and 425 or other features on the valve actuators and/or cassette body 310 may be arranged to ensure a compression seal when the valve is closed that is secure up to 40 pound per square inch (psi). Various examples of valve/valve actuator features that may be provided are discussed hereinafter in connection with, for example, FIGS. 10E-11E.

Figure 6A:
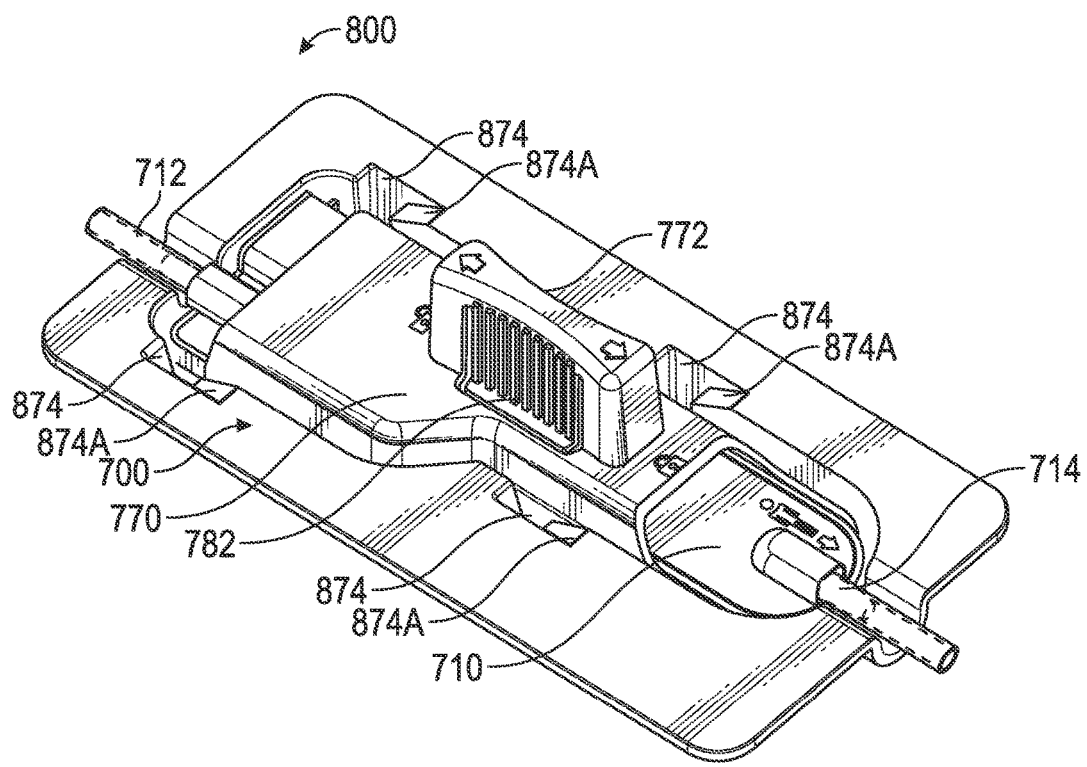
FIG. 6A illustrates perspective views of examples of a fourth embodiment disposable IV pump cassette and cassette recess, in accordance with aspects of the present disclosure.
Figure 6B:
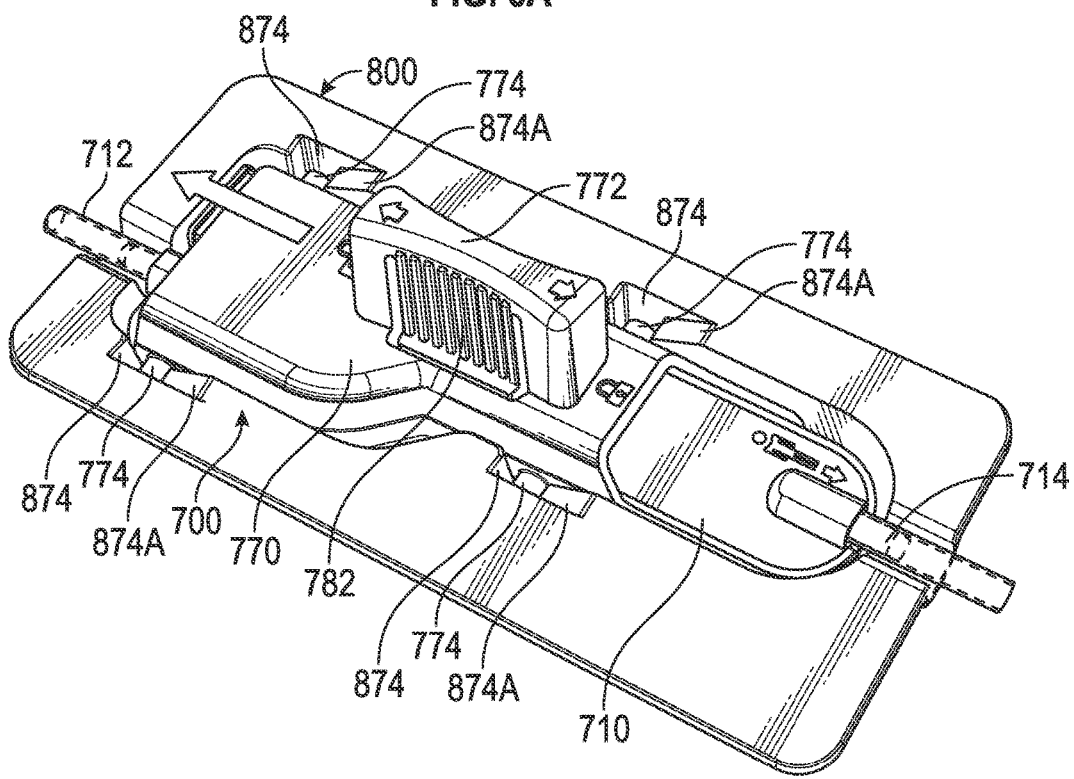
FIG. 6B illustrates perspective views of examples of a fourth embodiment disposable IV pump cassette and cassette recess, in accordance with aspects of the present disclosure.

FIGS. 6A and 6B illustrate examples of cassette 700 within cassette recess 800 in accordance with certain embodiments. Cassette 700 and cassette recess 800 may have similar components and features as like numbered components and features in other example embodiments described herein.

The plurality of protrusions 774 on slider 770 may be engaged with the plurality of slots 874 of cassette recess 800 such that cassette 700 is secured within cassette recess 800 for operation. Cassette recess 800 may configured to receive the pump cassette such that each of the plurality of protrusions 774 may contact a respective flat face ramp portion 874a of each of the plurality of cassette engagement slots 874. The plurality of protrusions 774 may contact and slide along the respective flat face ramp portions 874a to engage with the other portions of the cassette engagement slots 874 (e.g., the deeper portions of the L-channel). In some embodiments, each of the plurality of protrusion 774 may also comprise a flat face portion 774a (FIG. 6A) such that each flat face portion 774a may contact and slide along the respective flat face ramp portion 874a.

Figure 7A:
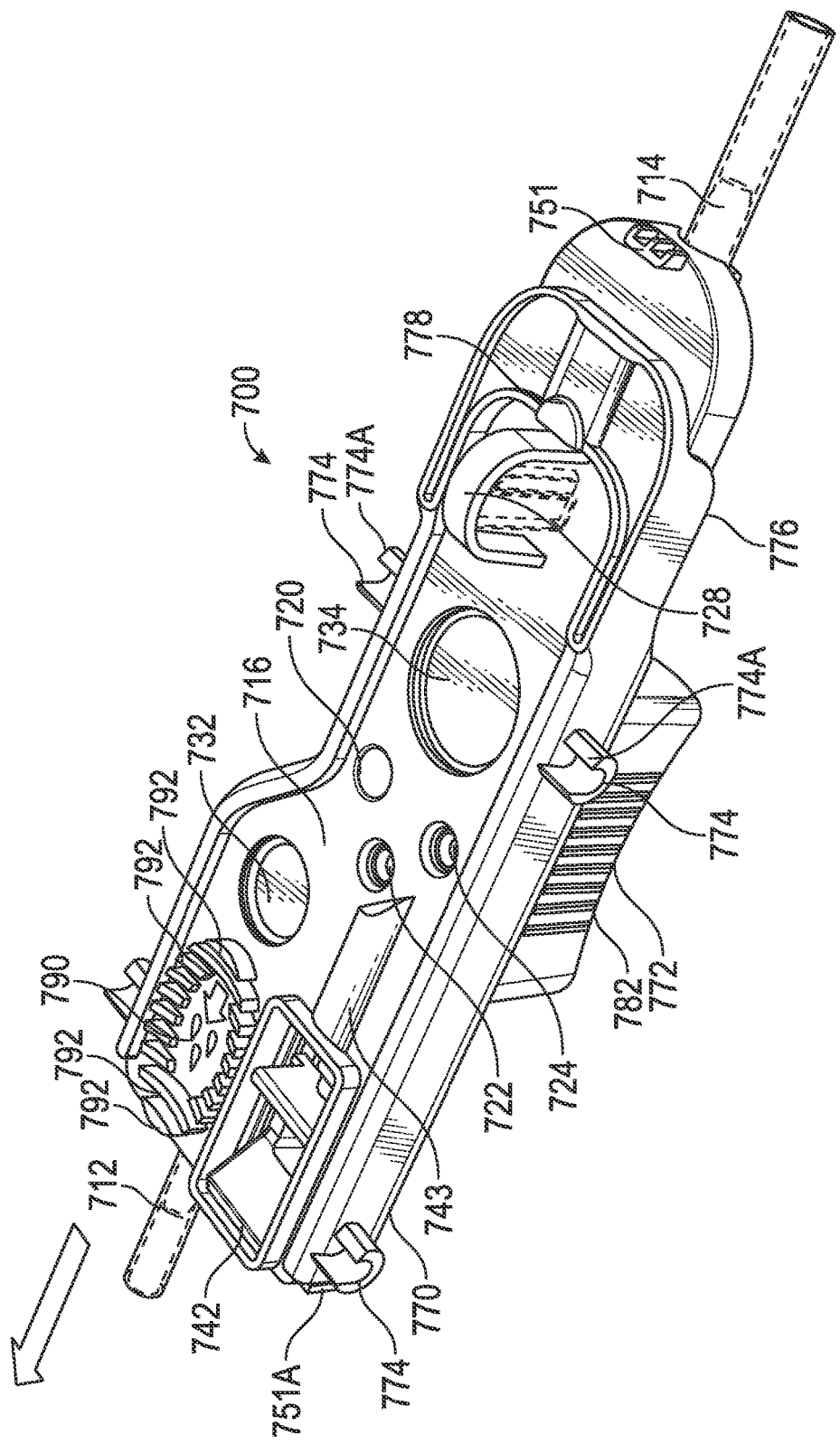
FIG. 7A illustrates perspective views of an example of a fourth embodiment disposable IV pump cassette, in accordance with aspects of the present disclosure.
Figure 7B:
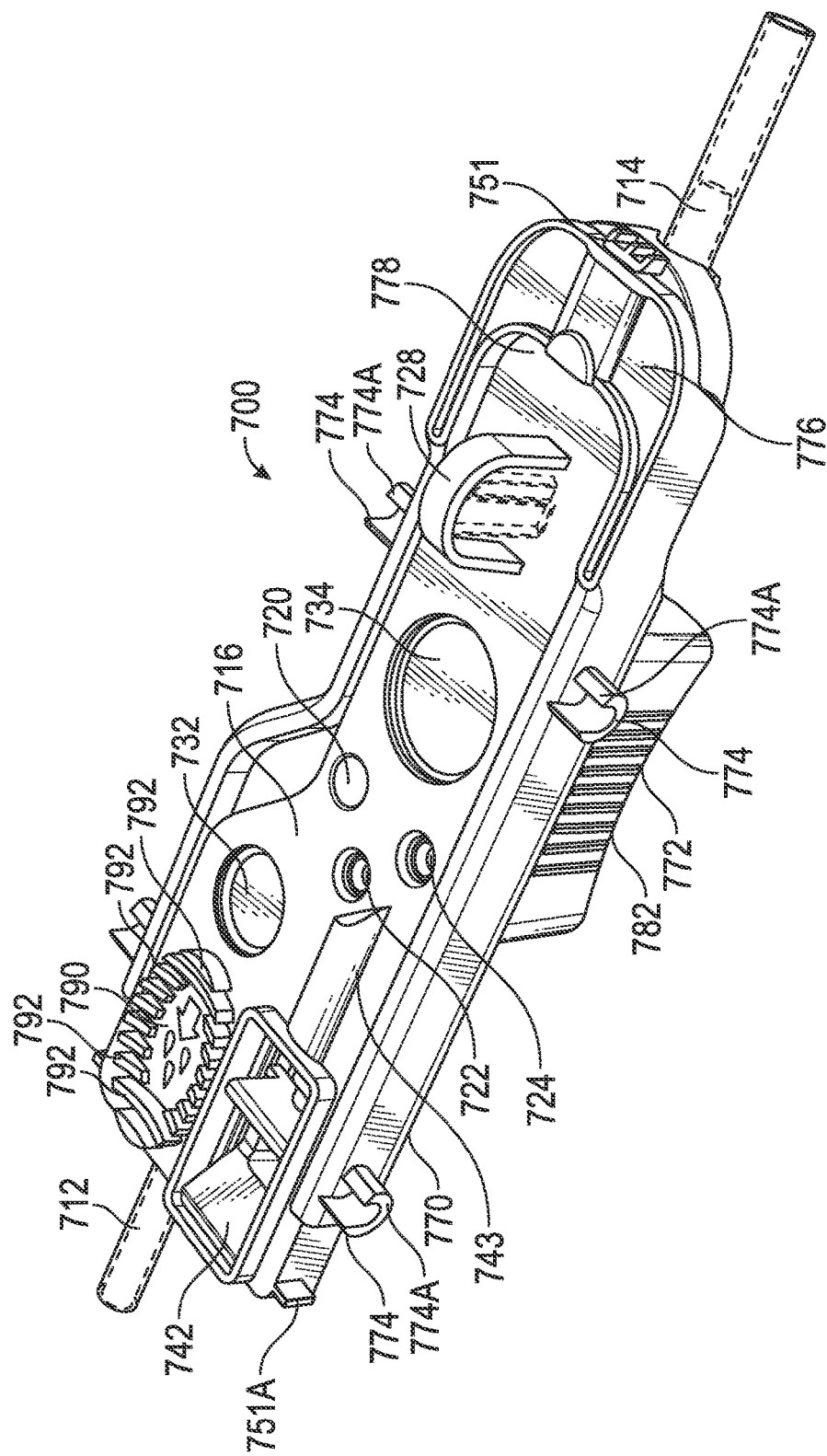
FIG. 7B illustrates perspective views of an example of a fourth embodiment disposable IV pump cassette, in accordance with aspects of the present disclosure.

With reference to the example cassette engagement positions of FIGS. 6A and 6B, other aspects of cassette 700 are provided with additional reference to the examples of FIGS. 7A and 7B. For example, flow stop valve 764 may be configured to restrict and/or regulate fluid flow proximal to outlet 714 of cassette body 710. Cassette 700 may include an inlet 712. In some embodiments, slider 770 may be articulated from a first position (e.g., slider 770 oriented toward top of cassette body 710) to a second position (e.g., slider 770 oriented toward bottom of cassette body 710) after priming and/or staging procedures have been completed and cassette 700 is to be installed into cassette recess 800. During insertion of cassette 700, cassette body 710 may be generally aligned with cassette recess 800 and the flat face portions 774a of the plurality of protrusions 774 may contact the respective flat face ramp portions 874a of the cassette engagement slots 874.

With reference to FIGS. 7A and 7B, slider 770 can be articulated between the first position and second position with respect to cassette body 710 such that flow stop valve 764 is actuated by one or more portions of the slider 770. For example, flow stop valve 764 may be actuated by contact with interface-facing slider section 776 when the slider 770 is in the first position. Thus, fluid flow through the fluid pathway may be occluded in the first position. Flow stop valve 764 may be activated by contact with interface-facing slider section 776 when the slider 770 is in the first position. Thus, fluid flow through the fluid pathway may be occluded in the first position. When the slider 770 is positioned in the second position, a portion of interface-facing slider section 776 (e.g., stop valve guard 778) does not contact flow stop valve 764 (or alternatively does not contact flow stop valve 764 sufficiently to activate flow stop valve 764), and flow stop valve 764 operates to allow fluid to flow freely through flow stop valve 764 to outlet 714.

Furthermore, slider 770 may be articulated between the first position and the second position when cassette 700 is not engaged with cassette recess 800 with the aid of grip feature 790. In certain embodiments, grip feature 790 may be arranged on an exterior surface of interface-facing frame portion 716 of cassette body 710, and may be defined in part by a plurality ribs 792 extending from the exterior surface of the interface-facing portion 716. However, in some embodiments, grip feature 790 may include a recessed portion extending into the exterior surface of interface-facing frame portion 716 (e.g., an indentation on the exterior surface that does not extend beyond a thickness of interface-facing frame portion 716). Grip feature 790 may be generally oval-shaped indicative of a thumb or finger support for a user or caregiver, for example.

Various features may be defined in or along the fluid pathway, in accordance with certain embodiments. For example, beginning from inlet 712, the fluid pathway may include features such as, but not limited to, upstream pressure dome 732 (e.g., an inlet-side compliant reservoir), inlet-side valve 722, outlet-side valve 724, downstream pressure dome 734 (e.g., an outlet-side compliant reservoir), and fluid pathway extension member 728. Other features that are not in or along the fluid pathway, but are disposed on cassette body 710, may include positioning port 720 and slider stopper 751. Pump drive mechanism 742 can be slidably engaged within piston guide 743.

Figures 8A, 8B:
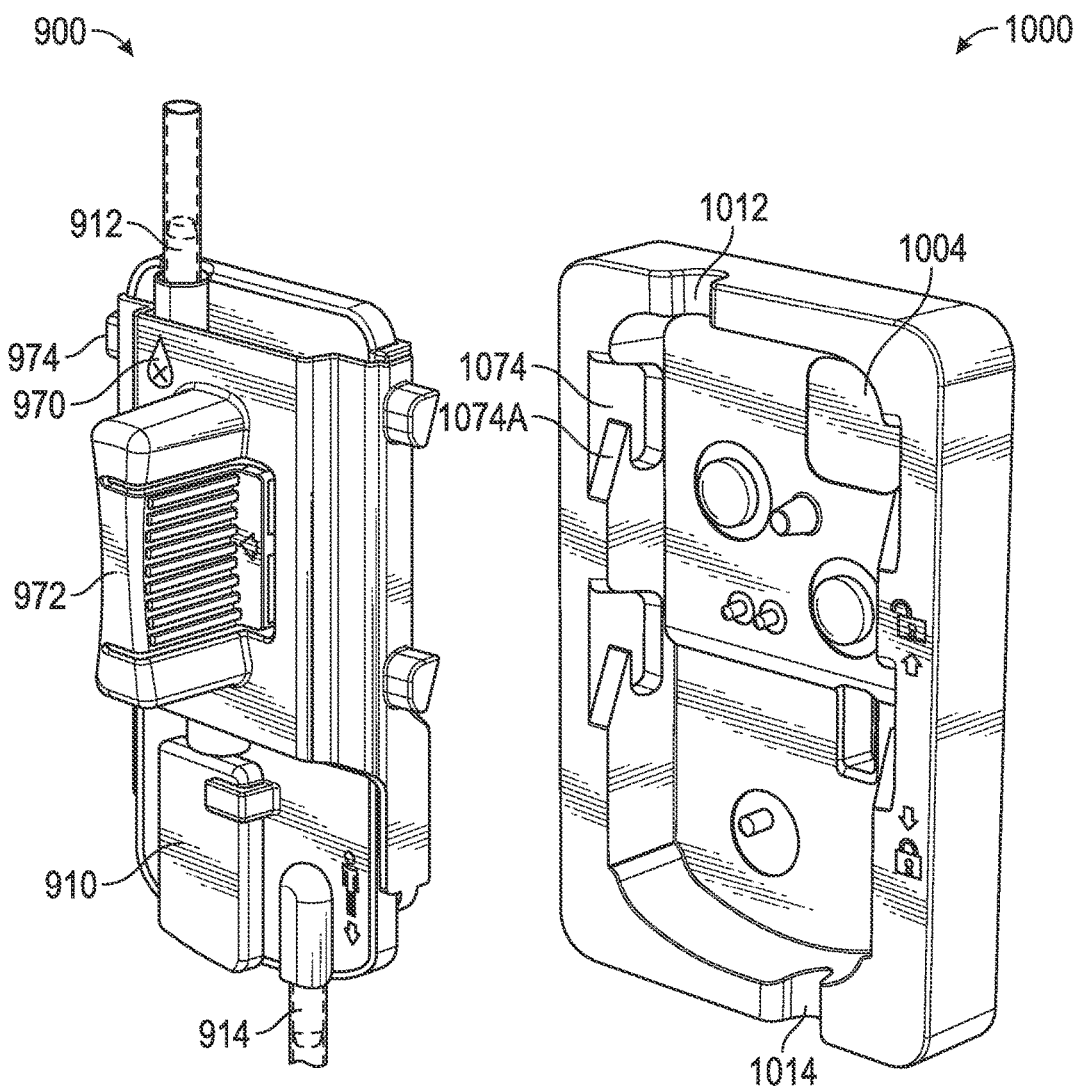
FIGS. 8A and 8B illustrate perspective views of examples of a fifth embodiment disposable IV pump cassette and cassette recess, in accordance with aspects of the present disclosure.
Figure 9A:
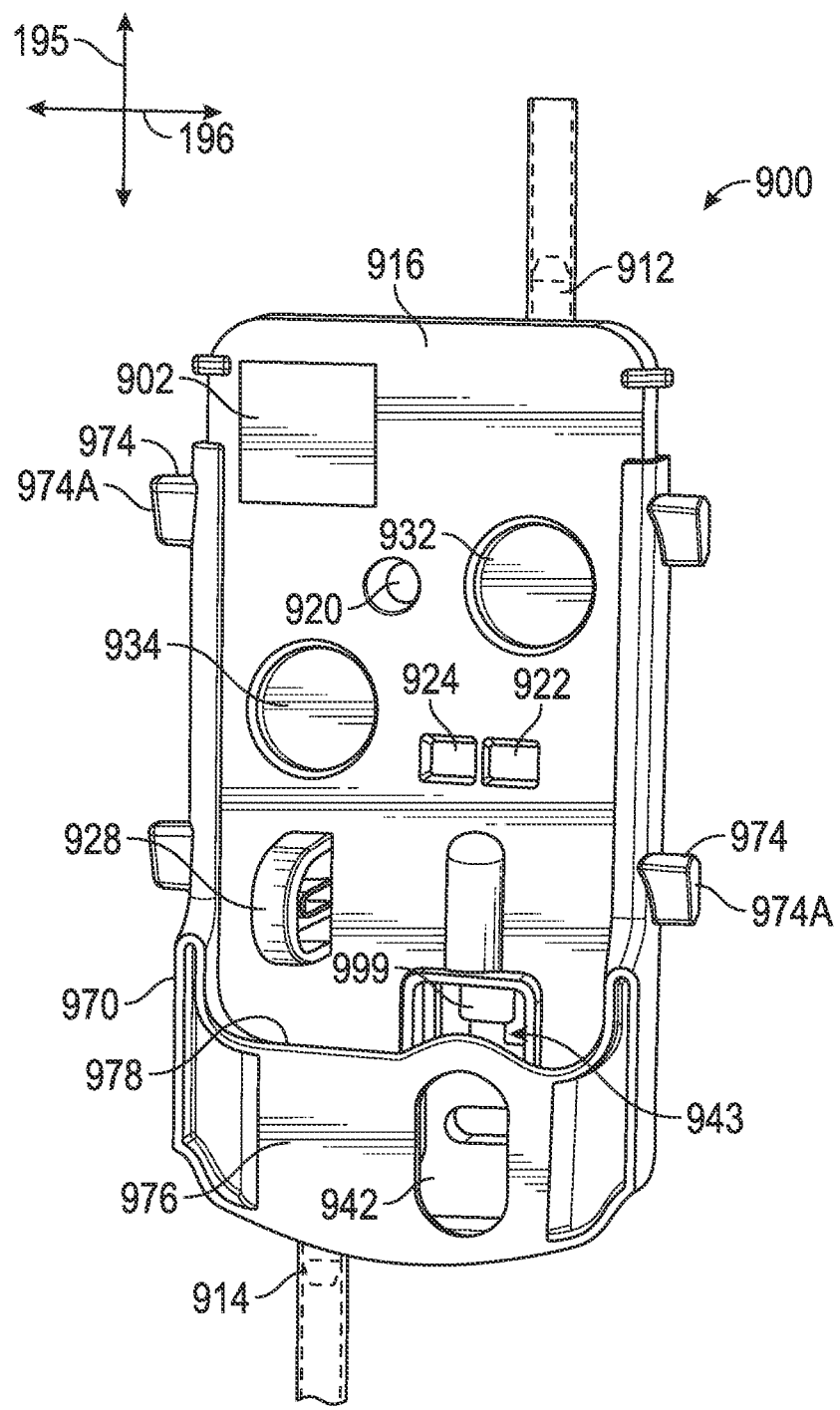
FIG. 9A illustrates a perspective view of an example of a fifth embodiment disposable IV pump cassette, in accordance with aspects of the present disclosure.

FIGS. 8A and 8B illustrate examples of a disposable IV pump cassette 900 and corresponding cassette recess 1000 of an interface module. In accordance with certain embodiments, cassette 900 may comprise a cassette body 910 and a slider 970. Cassette 900 may include certain may include certain visual indicators related to operation aspects of the cassette and the infusion pump system in general. For example, cassette may include identifiable images such as fluid drops indicating position of slider 970 for free-flow (e.g., flow stop valve 964 in an open position) and a patient figure proximal to outlet 914. In accordance with some aspects, one or more cassette-seated sensors may be disposed within the cassette recess 1000 so as to inform central processing unit 12 that the cassette is locked or secured into place within the cassette recess 1000 or seat. For example, cassette recess may include a window 1004 (or aperture) such that cassette identifier 902 (FIG. 9A) can be scanned. Cassette identifier 902 may include various information such as, but not limited to, a manufacturer, type, and use parameters of cassette 900. Moreover, cassette identifier 902 may be disposed on a top half of the exterior surface of interface-facing frame portion 916 with respect to gravity during use. Thus, a bottom half of the exterior surface of interface-facing frame portion 916 can be reserved for pump drive assembly and flow stop valve features, in accordance with certain embodiments. Cassette recess 1000 may include non-vertically aligned inlet recess 1012 and outlet recess 1014.

Slider 970 can be fixably and slidably engaged with cassette body 910 such that slider 970 may articulate longitudinally with respect to cassette body 910, but will be constrained within range of sliding motion such that the slider remains coupled to the cassette body 910. Slider 970 may be formed from rigid plastic or polymer material having lubricating characteristics (e.g., incorporating silicon or polytetrafluoroethylene (PTFE) additives), and is clear or translucent in accordance with certain embodiment. In some embodiments, slider 970 may be polycarbonate. In accordance with certain aspects, slider 970 may be lockable at one or more positions, and may include a slider grip 972 for unlocking and articulating slider 970. Slider 970 may also include a plurality of protrusion 974 or lugs that are configured to mate and be releasably lockable with a plurality of slots 1074 of the cassette recess 1000 (e.g., L-shaped locking channels).

Each of the plurality of protrusion 974 may also comprise a flat face portion 974a that is configured to interface with a respective flat face ramp portions 1074a of the cassette engagement slots 1074. In this regard, cassette 900 can be self-guided and self-latched into the cassette recess 1000. Accordingly, a door or lever action is not required in order to retain the cassette 900 within the cassette recess 1000.

Additionally, an overall size of cassette 900 and cassette recess 1000 may be reduced, in accordance with some aspects. For example, in certain embodiments, cassette body 910 may extended longitudinally a length between 70 mm and 90 mm. For orientation reference with respect to the various views of the examples illustrated of FIGS. 8A and 8B, longitudinal axis or y-axis 195, latitudinal axis or x-axis 196, and depth axis or z-axis 197 are provided as a reference on certain figures (e.g., FIGS. 9A and 10A-10D).

Various types, placement, and orientations of the plurality of protrusions 974 disposed on slider 970 are contemplated in the present disclosure. Aspects of the various cassette-coupling techniques illustrated in the example cassette embodiments 100, 300, 700 described herein may be further combined and arranged into additional configurations suitable for specific implementations given the benefit of the present disclosure.

Moreover, in accordance with certain aspects, features of cassette recess 1000 are designed to avoid wear down and/or risk of malfunction. For example, the plurality of slots 1074 arranged within cassette recess 1000 may be devoid of any movable latching mechanism in certain embodiments as such movable latching mechanisms may be susceptible to excessive wear and mechanical failure over repeated use with multiple disposable IV cassettes 900.

In operation, cassette 900 can be loaded directly into cassette recess 1000. In this regard, the direct loading of the cassette 900 will enable avoidance of shear forces that might otherwise be applied to the sensors, alignment features, and other engaging interfaces of cassette-facing surface 1016 of cassette recess 1000 from interaction with the interface-facing side of cassette body 910 as it is loaded into cassette recess 1000. It is to be understood that modification to the various features of cassette 900 can be made to accommodate the various cassette-coupling techniques disclosed herein.

Figure 9B:
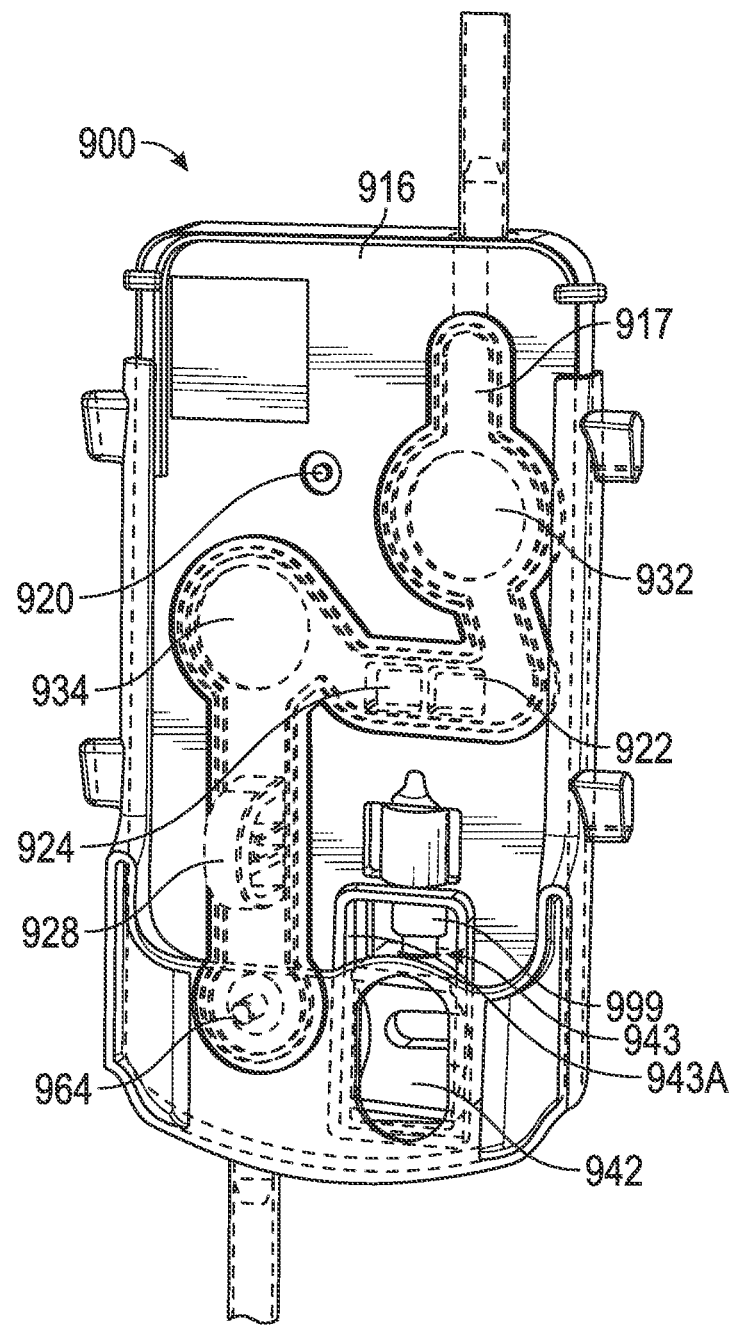
FIG. 9B illustrates a perspective view of an example of a fifth embodiment disposable IV pump cassette, in accordance with aspects of the present disclosure.

Cassette body 910 may comprise interface-facing frame portion 916 and slider-facing base portion 919 (FIGS. 9A and 9B) with membrane 917 disposed substantially therebetween. Portions of membrane 917 may extend through or be accessible from some openings of frame portion 916 (e.g., upstream pressure dome 932, downstream pressure dome 934, inlet-side valve 922, and outlet-side valve 924). In accordance with certain embodiments, membrane 917 can be a compliant material co-molded to the frame portion 916 and sealingly engaged with base portion 919 for defining a fluid pathway through cassette body 910 from inlet 912 to outlet 914. Mating edges of frame portion 916 and base portion 919 may be connected by fusing, welding, gluing, or the like. Membrane 917 and base portion 919 may further define a plurality of other features, some of which may be accessed through openings in frame portion 916.

Frame portion 916, membrane 917, and/or base portion 919 may define features in or along the fluid pathway, in accordance with certain embodiments. For example, beginning from inlet 912, the fluid pathway may include features such as, but not limited to, upstream pressure dome 932 (e.g., an inlet-side compliant reservoir), inlet-side valve 922, pump chamber 925, outlet-side valve 924, downstream pressure dome 934 (e.g., an outlet-side compliant reservoir), fluid pathway extension member 928, and flow stop valve 964. Other features that are not in or along the fluid pathway, but are disposed on cassette body 910, may include positioning port 920 and slider stopper 951.

Figure 9C:
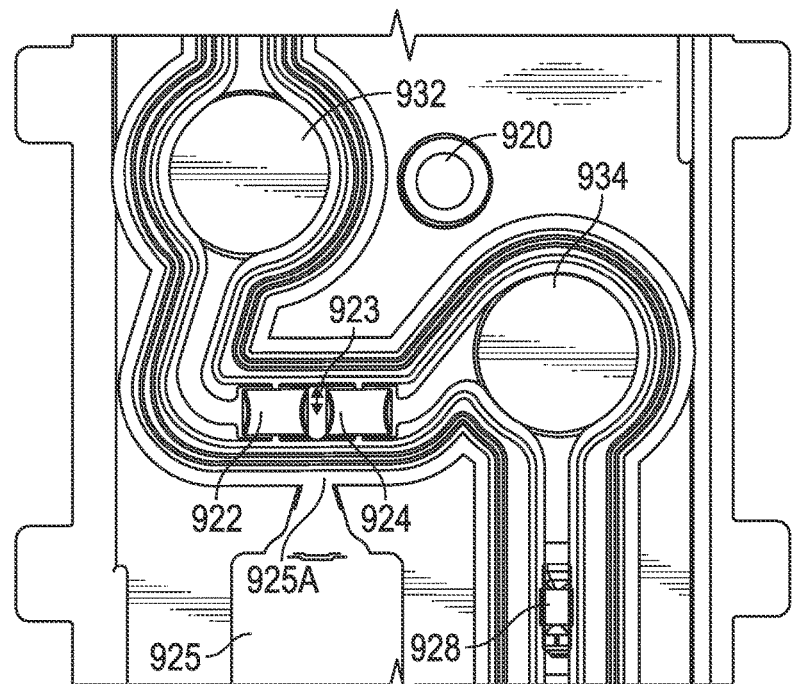
FIG. 9C illustrates an enlarged cross-sectional perspective view of an example of a fifth embodiment disposable IV pump cassette, in accordance with aspects of the present disclosure.
Figure 9D:
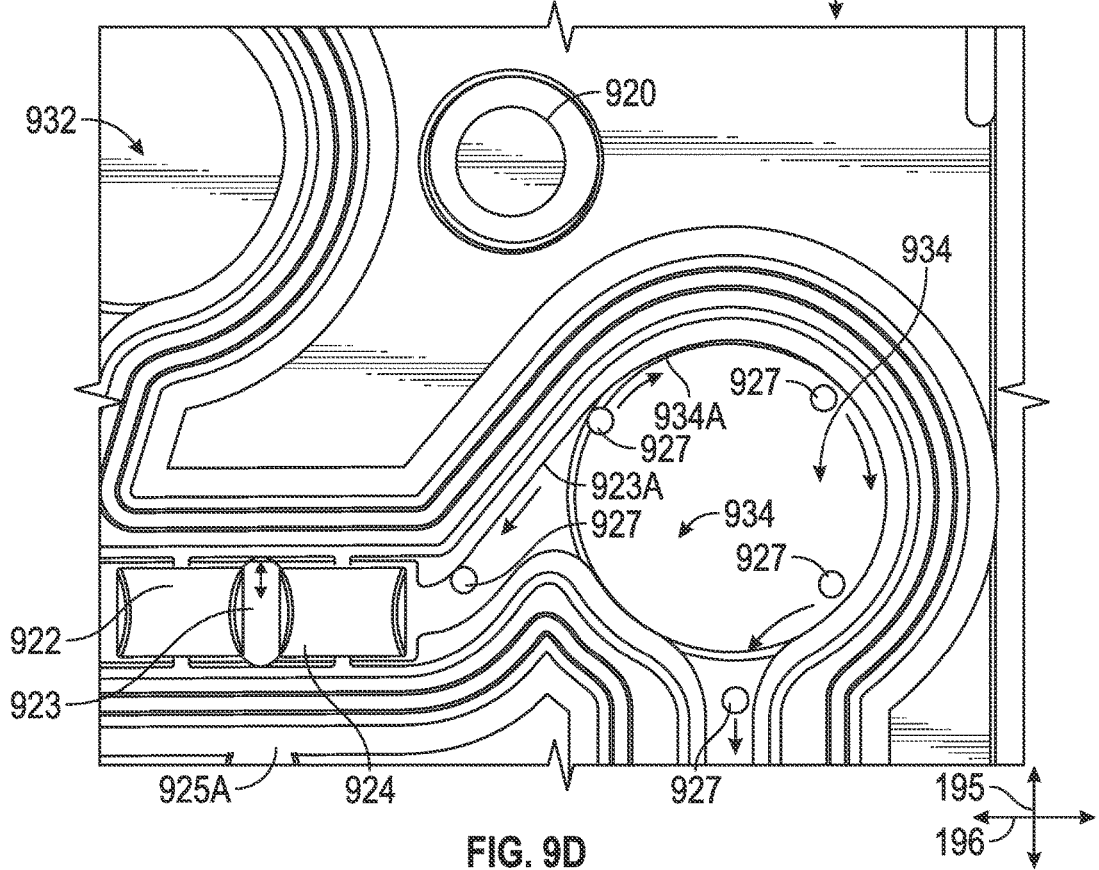
FIG. 9D illustrates an enlarged cross-sectional perspective view of an example of a fifth embodiment disposable IV pump cassette, in accordance with aspects of the present disclosure.
Figure 9E:
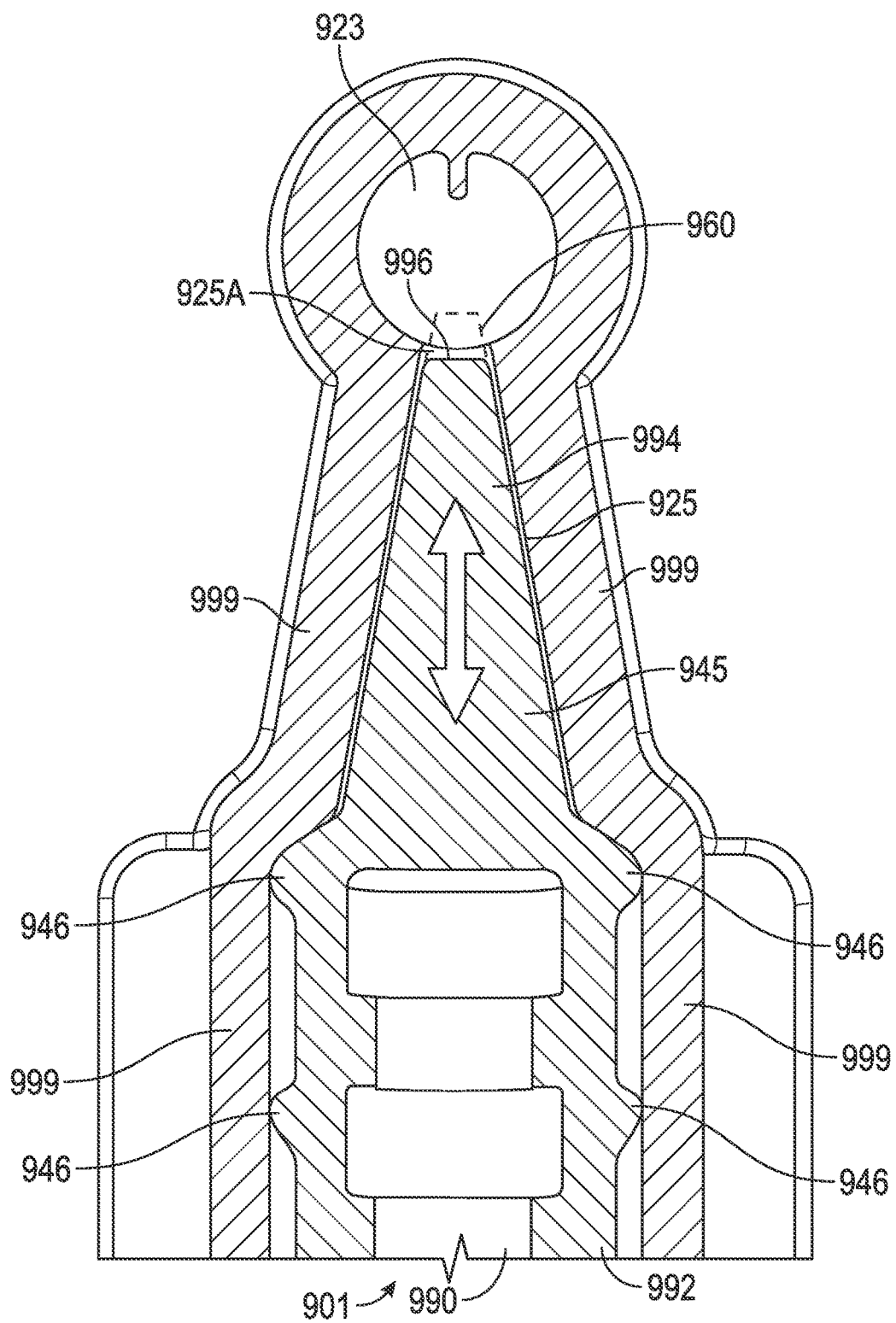
FIG. 9E illustrates an enlarged cross-sectional perspective view of an example of a fifth embodiment disposable IV pump cassette, in accordance with aspects of the present disclosure.

FIGS. 9C-9E are enlarged, longitudinal cross-sectional views of cassette body 910 proximate to pump chamber 925. Opening 925a of the pump chamber 925 (e.g., when piston head portion 945 is retracted) is disposed between the inlet-side valve 922 and outlet-side valve 924 along a bottom the fluid pathway section 923. In some embodiments, the nose or tip 996 of the piston head portion 945 is substantially aligned with a bottom of fluid pathway section 923 (FIG. 5E) to eliminate any dead space (e.g., internal space where air may accumulate) in pump chamber 925 as well as reduce any drag associated with the fluid flow through the fluid pathway section 923. Thus, in some embodiments, the dead space is less than 1% of the total volume of the pump chamber 925. For example, in certain embodiments, the volume of the pump chamber is 80 microliters when the piston head portion 945 is fully retracted in its reciprocating cycle.

As indicated by dashed line 960 (FIG. 5E), in some embodiments, the nose or tip of the piston head portion 945 may optionally be configured to extend, in a forward-most position, into the fluid pathway 923. A piston head portion having a nose or tip that extends into the fluid pathway may increase the amount of air that is pushed out of the pump chamber in a pumping cycle.

In this regard, it can be advantageous to place the inlet-side valve 922 and outlet-side valve 924 close together along the fluid pathway section 923 proximal to the pump chamber 925. For example, a distance between the inlet-side valve 922 and outlet-side valve 924 is approximately between 4 millimeters and 7 millimeters in some embodiments. In this way, any dead space (e.g., internal space where air may accumulate) within the pump chamber between inlet-side valve 922 and outlet-side valve 924 may be reduced or eliminated. Moreover, by placing the inlet-side valve 922 and outlet-side valve 924 close together along the fluid pathway section 923 proximal to the pump chamber 925, any stress across the system generated by the actuation of valve actuators 1022 and 1024 may be more evenly distributed across the system (in comparison with stresses generated at different locations by widely separated actuators/valves), thereby improving the lifetime and reducing the risk of damage or failure in the system. It is to be appreciated that piston pump techniques can provide repeatedly precise positive displacement of fluid in the pump chamber 925.

In accordance with certain embodiments, a section or tract of the fluid pathway leading from the area of the outlet-side valve 924 may comprise a straight edge portion 923a that is tangent to an arcuate edge 934a of the downstream pressure dome 934. The tangentially aligned straight edge 923a and arcuate edge 934a are top edge portions with respect to an orientation of the cassette 900 with respect to gravity, for example, as the cassette 900 would be installed into cassette recess 1000 such that longitudinal axis or y-axis 195 is substantially aligned with gravity.

For example, if air bubbles enter an IV set including a pump cassette, the air bubbles generally have a tendency to rise with respect to gravity within the fluid being moved through the fluid pathway within such a cassette. Thus, as illustrated in the example of FIG. 13D, if one or more air bubbles 927 enter the fluid pathway of the cassette body 910, the one or more air bubbles 927 are more likely to be flushed out of downstream pressure dome 934 as a force from the fluid exiting the opening 925a of pump chamber 925 along the bottom of fluid pathway section 923 will be substantially applied proximal the perimeter of the downstream pressure dome 934 as fluid will flow along the tangentially aligned straight edge 923a and arcuate edge 934a moving the one or more air bubbles 927, which may initially rise to the top of the downstream pressure dome 934, around the perimeter and out of the downstream pressure dome 934.

With respect to the orientation of pump chamber 925 of cassette 900 and pump chamber having pump chamber opening/access 125 of cassette 100, in certain embodiments, it may be advantageous to have pump chamber 925 in order to prevent or limit the impact of air bubbles in pump chamber accuracy. For example, in pump chamber having pump chamber opening/access 125 during the delivery phase of the pump cycle, fluid will be expelled first and any air that accumulates in the pump chamber of cassette 100 and between the inlet-side valve 122, outlet-side valve 124 will remain thereby decreasing pumping accuracy of the system. In contrast, pump chamber 925 of cassette 900 will first expel any air that is in the pump chamber, thereby preventing air from accumulating in the pump chamber 925 and in the region between the inlet-side valve 922, outlet-side valve 924 and maintaining accuracy. For example, with additional reference to the example of FIG. 9G, one or more fluid sensors may be disposed within sensor slot 1028. The one or more fluid sensors disposed within sensor slot 1028 can be ultrasonic sensors configured as an air-in-line detector, for example. In certain embodiments, extension member 928 may be disposed on cassette body 910 and positioned along the fluid pathway between downstream pressure dome 934 and flow stop valve 964. However, in some embodiments, extension member 928 can be positioned at other locations along the fluid pathway such as, but not limited to, between inlet 912 and upstream pressure dome 932. Additionally, in other embodiments, a plurality of extension members 928 with a plurality of corresponding sensor slots 228 may be positioned along a fluid pathway of cassette body 910.

With reference to the examples illustrated in FIGS. 9A-9G, cassette body 910 may include a piston 901 as a pump drive assembly in accordance with certain embodiments. The piston may be longitudinally movable or with respect to the rigid body of pump cassette 900. For example, the piston may include an actuator-receiving portion 942 as a pump drive mechanism for receiving pump actuator 1042 of cassette recess 1000. Actuator-receiving portion 942 may include opposing ramp portions 942a and an elongate slot 942b. In certain embodiments, elongate slot 942b may be arranged orthogonal to the movement of the piston. Actuator-receiving portion 942 can be operatively coupled to piston head portion 945 slidably positioned or engaged within piston guide 943 or casing (e.g., generally cylindrical or frustoconical casing) such that reciprocal movement of piston head portion 945 may urge fluid into and out of the pump chamber 925 and through the fluid pathway of cassette body 910. The piston guide 943 or other portions of the frame portion 916 and/or base portion 919 may include guideslots 943a (e.g., see FIGS. 9B and 9F) that are received by guiderails 942c on the actuator-receiving portion 942 for prohibiting rotational movement of the piston within the rigid body.

Figure 9F:
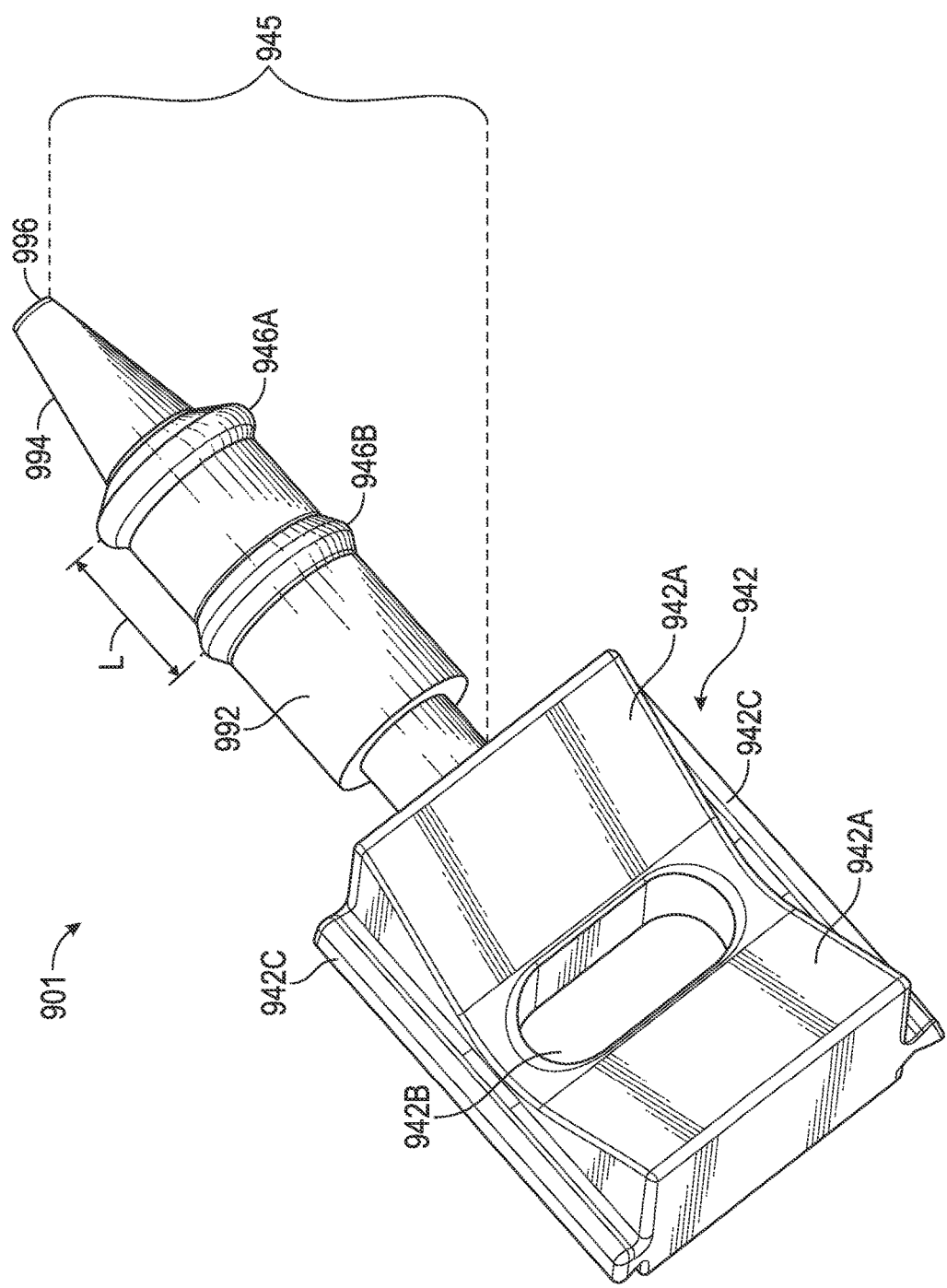
FIG. 9F illustrates an enlarged perspective view of an example of a piston of a disposable IV pump cassette, in accordance with aspects of the present disclosure.

The pump chamber 925 may be defined by a portion of the piston guide 943 or casing 999 distal from the actuator-receiving portion 942 that is adjacent to and fluidly coupled with a tract or section of the fluid pathway between inlet-side valve 922 and outlet-side valve 924. Piston head portion 945 may comprise one or more slidable seals 946. Based on the stroke of the piston and the position of the innermost seal 946 along the piston's path as piston head 945 moves, the innermost seal 946 may define the boundary of a changeable volume portion of the pump chamber during reciprocal movement of piston head portion 945 slidably disposed within the piston barrel 999. For example, piston head portion 945 may comprise a first seal 946a proximal to a tip end of the piston head portion 945. The first seal 946a can provide a sealed movable barrier of the pump chamber 925. Piston head portion 945 may also comprise a second seal 946b distal from the tip end with respect to the first seal 946a. The second seal 946b can provide a sealed movable exterior-facing barrier that prevents any substances (e.g., dirt, dried fluid particles or pathogens (airborne or not), or any other substance, particle, or microorganism) near the cassette 900 from contacting the first seal 946a. In this way, such substances can be prevented from direct contact with the first seal 946a that may compromise the sealed movable barrier of the pump chamber 925. In certain embodiments, the first seal 946a is disposed on sealing member 992 at a specific distance L from the second seal 946b such that the path of second seal 946b within piston barrel 999 does not overlap the path of seal 946a in the piston barrel. For example, the distance L may be longer than the stroke of the piston so that seal 946a does not contact any portion of the surface of the piston barrel that is contacted by seal 946b. In this way, seal 946a may be prevented from contacting any debris (e.g., dirt, dried fluid particles or pathogens (airborne or not), or any other substance, particle, or microorganism) from seal 946b. In certain embodiments, the first seal 946a and the second seal 946b are circumferential as shown in FIGS. 9E and 9F.

The volume in pump chamber 925 changes with the reciprocal motion of the piston head portion 945 such that a volume of the pump chamber 925 may be varied by movement of the piston head portion 945 in accordance with certain embodiments.

As shown in FIG. 9E, piston head portion 945 may include a center post 990 and a sealing member 992. Sealing member 992 may be integrally formed on center post 990 (e.g., by forming center post 990 and sealing member 992 from a common material in an injection molding process or from different materials in a two-shot injection molding process) or sealing member 992 may be formed separately from center post 990 and may be configured to be installed onto center post 990 (e.g., by pressing or snapping sealing member 992 onto center post 990). In accordance with an embodiment, center post 990 may extend from and be integrally formed with actuator-receiving portion 942. Sealing member 992 may be formed from the same material as center post 990 or from a different material. For example, sealing member 992 may be formed from a relatively softer material such as a silicon-based material that facilitates forming a slidable seal between each of seals 946 and the interior wall of a pump chamber such as pump chamber 925. Seals 946 of piston head portion 945 may be integrally formed portions of sealing member 992 (e.g., circumferential protrusions extending around the cylindrical or conical circumference of member 992).

In certain embodiments, a second seal 946b may be positioned within or proximal to piston guide 943 and slidably engaged with piston head portion 945 thereby reducing the possibility of any substances (e.g., dirt or dried fluid particles) near the cassette 900 from contacting one or more slidable seals of the piston head portion 945. The one or more slidable seals 946 of the piston head portion 945 may contact an internal wall piston guide 943 to form a movable barrier of the pump chamber 925. Additionally, piston head portion 945 may include a tip portion 994 having a reduced cross-sectional measurement or dimension for more precise volumetric displacement of fluid into and out of pump chamber 925.

For example, pumping operation of infusion pump system 10, 11 when cassette 900 is primed and seated in cassette recess 1000 may comprise activating outlet-side valve actuator 1024 such that outlet-side valve 924 is closed or sealed while activating inlet-side valve actuator 1022 such that inlet-side valve 922 is opened. Opening of inlet-side valve 922 may coincide with or occur shortly after a reverse stroke of piston head portion 945 (e.g., a movement of piston head portion 945 away from pump chamber 925). Accordingly, fluid can flow from upstream pressure dome 932 to pump chamber 925. Alternatively, or in addition to, outlet-side valve 924 may comprise a one-way valve mechanism that permits flow of fluid under normal conditions in one direction (from a fluid container to a patient). Additionally, inlet-side valve 922 may also comprise a one-way valve mechanism permitting flow of fluid in one direction (from a fluid container to a patient) under normal operating conditions. In this configuration, cassette recess 1000 may not need to incorporate either outlet-side valve actuator 1024 or inlet-side valve actuator 1022. Outlet-side valve 924 and inlet-side valve 922 may limit flow of fluid in one direction, but permit flow in an opposite direction in the event fluid pressure overcomes a cracking pressure of the valves.

Continuing with the valve-operated implementation, pumping operation may comprise activating outlet-side valve actuator 1024 such that outlet-side valve 924 is open while activating inlet-side valve actuator 1022 such that inlet-side valve 922 is closed or sealed. Opening of outlet-side valve 924 may coincide with or occur shortly before a forward stroke of piston head portion 945 (e.g., a movement of piston head portion 945 toward the opening of the pump chamber 925 such that the volume of the pump chamber 925 is reduced). Thus, fluid can flow from pump chamber 925 to downstream pressure dome 934 and consequently urging fluid out outlet 914.

In certain embodiments, pump chamber 925 is a smaller volume than one or both of upstream pressure dome 932 and downstream pressure dome 934. Accordingly, larger and compliant upstream pressure dome 932 and/or downstream pressure dome 934 can address any backpressure issues in the IV set, thereby allowing for an accurate and precise volume of fluid entering pump chamber 925 to be pumped.

Referring to FIGS. 9A-9G, actuator-receiving portion 942 and pump actuator 1042 may be configured as a reciprocating motion mechanism (e.g., a scotch-yoke configuration) in certain implementations. Actuator-receiving portion 942 may be accessible by pump actuator 1042 via an aperture through interface-facing slider section 976. In such implementations, actuator-receiving portion 942 may include opposing ramp portions 942a for guiding a circularly rotatable pin 1052 of pump actuator 1042 toward the elongate slot 942b of actuator-receiving portion 942. For example, the outer edges of the opposing ramp portions may be arranged at a distance that will ensure engagement with the circularly rotatable pin 1052 of pump actuator 1042. When the rotatable pin 1052 contacts one of the ramp portions, the actuator-receiving portion 942 will move to align the elongate slot 942b of actuator-receiving portion 942 with the rotatable pin 1052 of pump actuator 1042. As such, the actuator-receiving portion 942 may be sized and positioned to receive the circularly rotatable pin 1052 at all positions of the circularly rotatable pin 1052 along a circular path. Additionally, the elongate slot 942b may have a width similar to the diameter of the circularly rotatable pin 1052.

However, it is to be appreciated that other pump drive assemblies are contemplated with cassette 900 and cassette recess 1000 in accordance with the present disclosure.

In certain embodiments, cassette recess 1000 may include an upstream pressure sensing probe 1032 and downstream pressure sensing probe 1034 enabling measurement of in-line pressure and fault isolation to a section of the fluid pathway. For example, upstream pressure sensing probe 1032 may operably contact upstream pressure dome 932 through a corresponding opening of interface-facing frame portion 916. Similarly, downstream pressure sensing probe 1034 may operably contact downstream pressure dome 934 through a corresponding opening of frame portion 916.

The x-y positioning of cassette 900 within cassette recess 1000 can be constrained by the positioning port 920 and positioning protrusion 1020 mating interface, as well as fluid pathway extension member 928 and sensor slot 1028 mating interface (e.g., air-in-line detector feature). In this regard, cassette 900 and cassette recess 1000 can have two points of contact in the z-axis direction (e.g., an axis through and transverse to a general plane of the interface-facing surface of cassette body 910 of cassette 900 and cassette-facing surface of cassette recess 1000) for interlock alignment of the cassette with respect to the x-y positioning of the interface side of the cassette body 910.

According to certain aspects, positioning port 920 may be located proximal to inlet-side valve 922 and outlet-side valve 924, and correspondingly mating positioning protrusion 1020 may be located proximal to inlet-side valve actuator 1022 and outlet-side valve actuator 1024. In this regard, the cassette 900 may be positioned properly without over constraining the cassette 900.

Figure 10A:
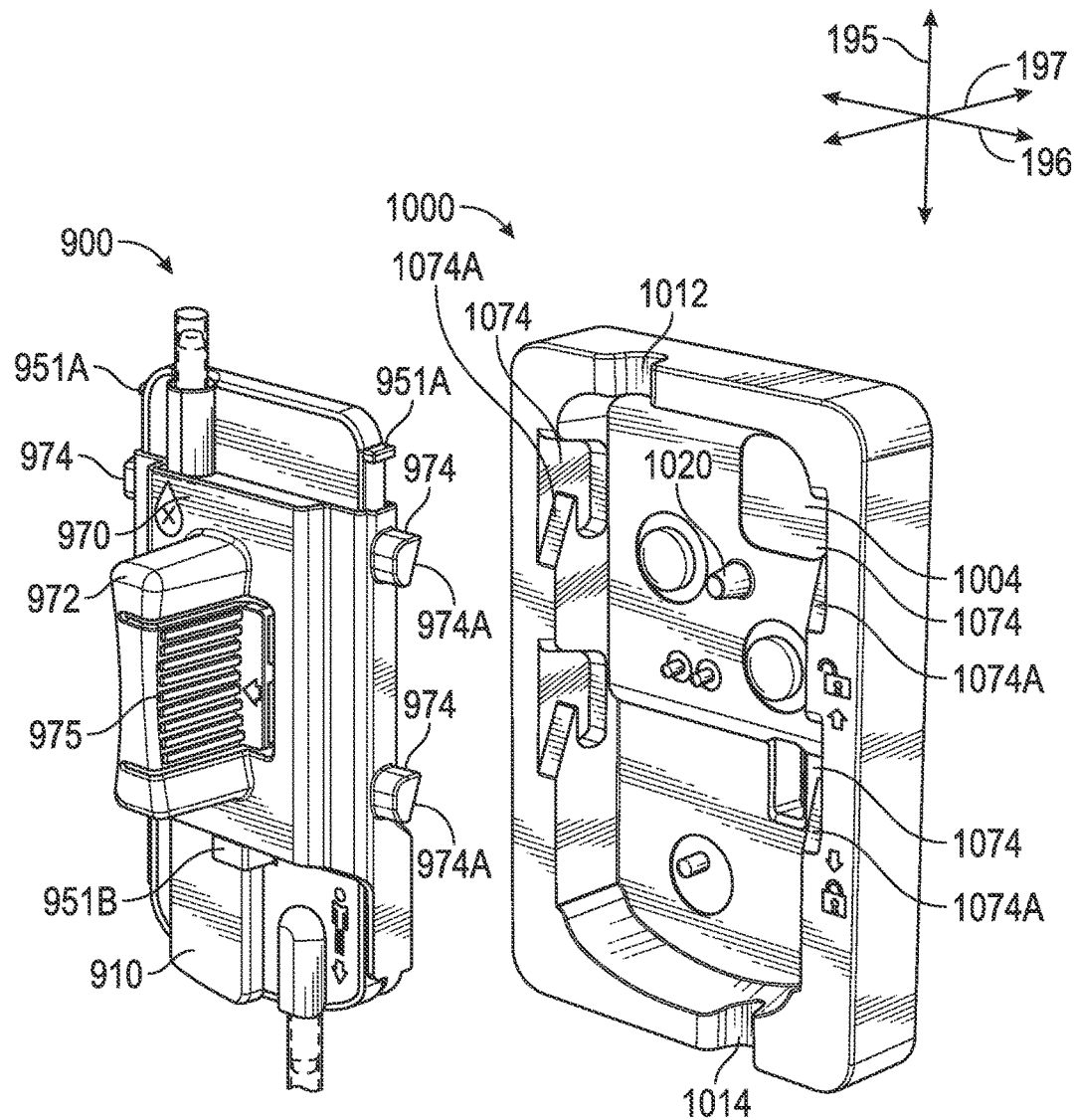
FIG. 10A illustrates perspective views of examples of a fifth embodiment disposable IV pump cassette and cassette recess, in accordance with aspects of the present disclosure.

FIGS. 10A-10D illustrate an example of a cassette engagement sequence with cassette 900 and cassette recess 1000. Cassette 900 may be aligned such that the plurality of protrusions 974 on slider 970 may be aligned along z-axis 197 for engagement with the plurality of slots 1074 of cassette recess 1000. In accordance with certain aspects, cassette 900 may have a longitudinal length along y-axis 195, a lateral width along x-axis 196, and a depth along z-axis 197. As illustrated in FIG. 10A and described herein, the depth of the cassette 900 may be a smaller dimension than either the length or the width of cassette 900. In this regard, cassette 900 is front loaded into cassette recess 1000.

Figure 10B:
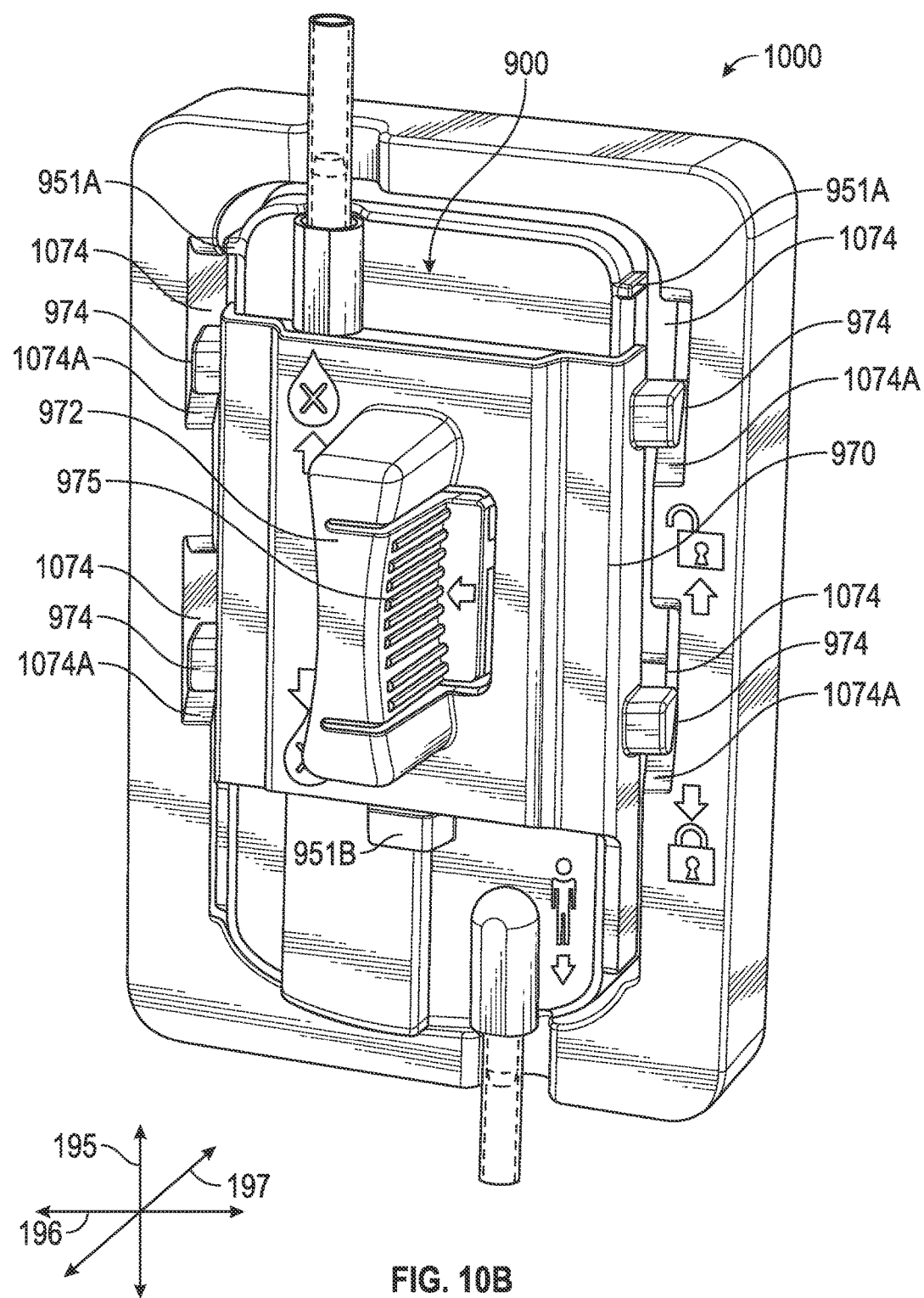
FIG. 10B illustrates perspective views of examples of a fifth embodiment disposable IV pump cassette and cassette recess, in accordance with aspects of the present disclosure.

As illustrated in FIGS. 10A and 10B, the plurality of protrusions 974 on slider 970 of cassette 900 may engage with the plurality of slots 1074 of cassette recess 1000 such that cassette body 910 may be generally aligned with cassette recess 100 and the flat face portions 974a of the plurality of protrusions 974 may contact the respective flat face ramp portions 1074a of the cassette engagement slots 1074 (e.g., slider 970 in the second position with respect to cassette body 910). In certain embodiments, the flat face portions 974a of the plurality of protrusions 974 may have an angled plane different from a general plane of the interface-facing surface of cassette body 910 of cassette 900 and cassette-facing surface 1016 of cassette recess 1000.

Figure 10C:
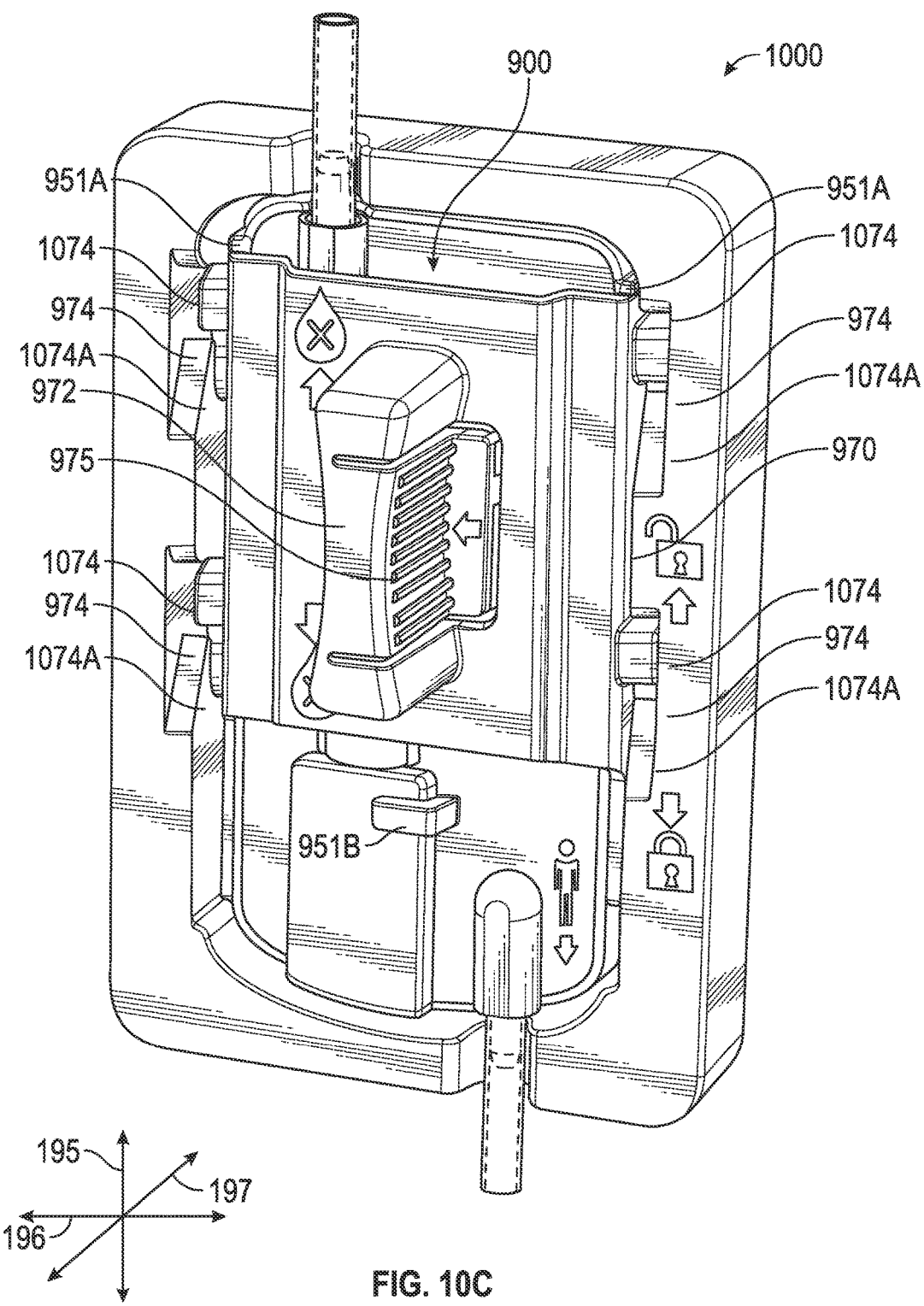
FIG. 10C illustrates perspective views of examples of a fifth embodiment disposable IV pump cassette and cassette recess, in accordance with aspects of the present disclosure.

Next, as illustrated in FIG. 10C, when a force is directed to the slider 970 substantially orthogonal to general plane of the interface-facing surface of cassette body 910 of cassette 900 and cassette-facing surface 1016 of cassette recess 1000, the slider 970 articulates in a direction from the second position to the first position. In this regard, the plurality of engagement protrusions 974 may slide along the respective flat face ramp portions 1074a of the cassette engagement slots 1074 deeper into the cassette recess 1000.

Figure 10D:
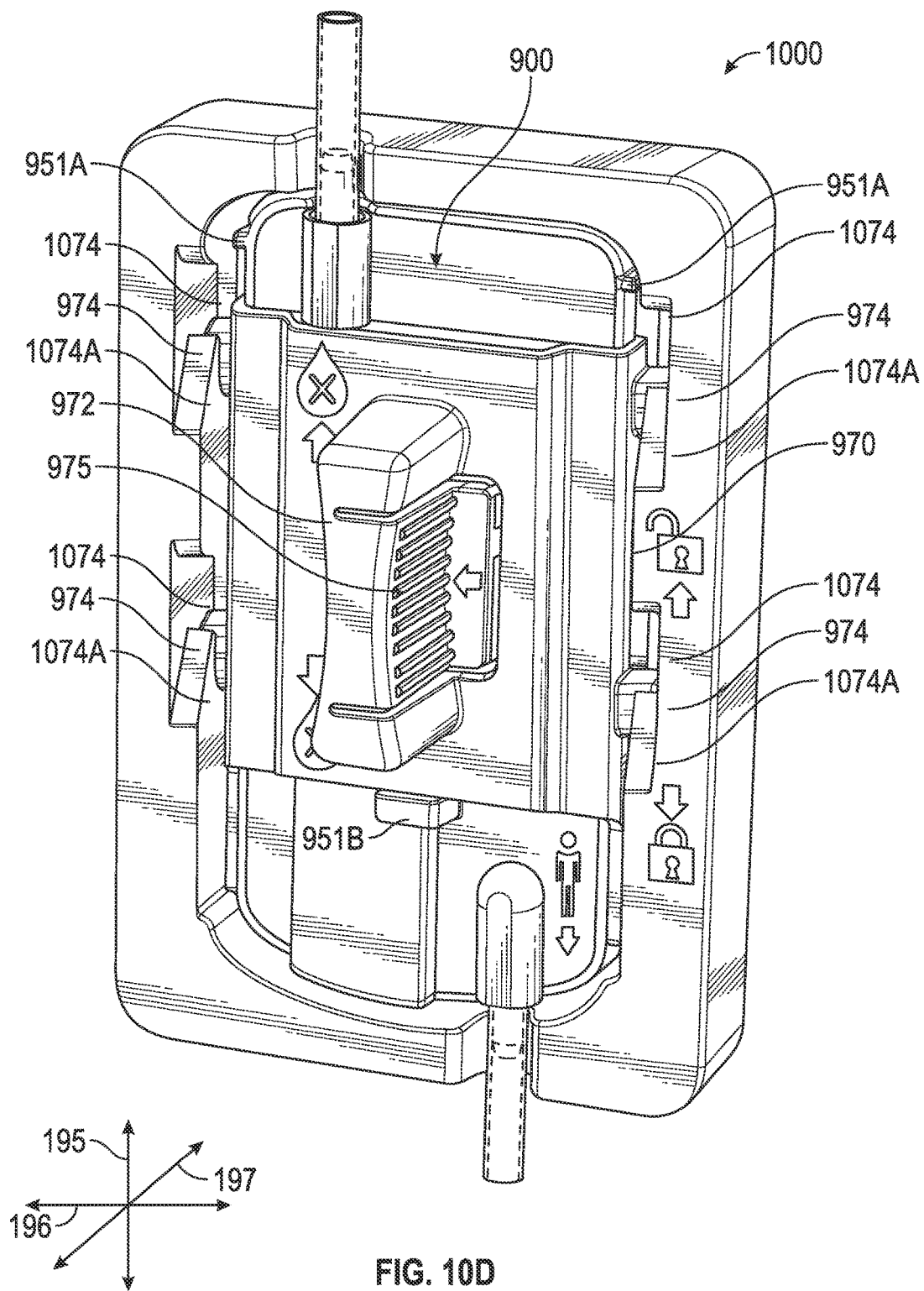
FIG. 10D illustrates perspective views of examples of a fifth embodiment disposable IV pump cassette and cassette recess, in accordance with aspects of the present disclosure.

Next, as illustrated in FIG. 10D, slider 970 may be longitudinally articulated along y-axis 195 such that cassette 900 is latched and locked by slider 970 within cassette recess 1000. For example, the plurality of engagement protrusions 974 may be positioned behind the flat face ramp portions 1074a of the cassette engagement slots 1074 while cassette 900 is engaged and operational with cassette recess 1000. It is to be noted that in some embodiments, loading of cassette 900 within cassette recess 1000 may be laterally oriented (e.g., 90° rotation of z-axis 197 so that x-axis 196 and y-axis 195 are switched).

In certain embodiments, flow stop valve 964 may be configured to restrict and/or regulate fluid flow proximal to outlet 914 of cassette body 910. In the first position, flow stop valve 964 is aligned under a portion (e.g., flat surface) of interface-facing slider section 976 of slider 970. When the slider 970 is positioned in the first position, the portion of interface-facing slider section 976 contacts and activates flow stop valve 964 such that fluid flow is occluded at that position of the fluid pathway proximal to outlet 914 cassette body 910. Therefore, fluid leakage can be avoided during the final preparation stages (e.g., after priming of cassette 900) and prior to the start of insertion stage into cassette recess 1000, in accordance with certain implementations. Moreover, in accordance with certain configurations, the first position of slider 970 may correspond to a position of cassette 900 for disengaging with cassette recess 1000.

Slider 970 can be articulated to a second position with respect to cassette body 910 (e.g., articulated downwardly in certain implementations). In this second position, cassette 900 will be latched within cassette recess 1000 by virtue of protrusions 974 being engaged with slots 1074 and locked by virtue of slider 970 with respect to cassette body 910. In the second position, flow stop valve 964 is aligned under a stop valve guard 978 (e.g., ramped, rounded, or recessed surface) of interface-facing slider section 976 of slider 970. When the slider 970 is positioned in the second position, the portion of interface-facing slider section 976 does not contact flow stop valve 964 (or does not contact flow stop valve 964 sufficiently to activate flow stop valve 964), and flow stop valve 964 operates to allow fluid to flow freely through flow stop valve 964 to outlet 914.

In accordance with certain embodiments, stop valve guard 978 may be positioned underneath a portion of and/or proximal to an edge along interface-facing slider section 976 of slider 970 such that when cassette 900 is securely latched or locked within cassette recess 1000 (e.g., in the second position), stop valve guard 978 is positioned above flow stop valve 964. In this regard, stop valve guard 978 can protect flow stop valve 964 from being inadvertently depressed and activated to restrict fluid flow while cassette 900 is in use. For example, a force applied to the slider side of cassette 900 while locked within cassette recess 1000 would not depress flow stop valve 964 as the lateral tolerances of the slidable coupling between cassette 900 and slider 970 are tighter than a distance between the inner surface of the stop valve guard 978 and an outer surface of the flow stop valve 964. In this regard, distances between stop valve guard 978 and flow stop valve 964 may be optimized such that anticipated forces applied to cassette 900 (e.g., from a user or caregiver inadvertently bumping cassette 900 or road vibrations in moving ambulance setting) may not cause an undesired activation of flow stop valve 964.

Similarly, when cassette 900 is to be disengaged from cassette recess 1000, slider 970 can be unlatched and/or unlocked from cassette recess 1000 by accessing grip 972, squeezing flexible portion 975 to unlock slider 970, and articulating slider 970 back to the first position with respect to cassette body 910. Some amount of force may be required by the user to articulate slider 970 to the first position as the plurality of protrusions 974 may be securely latched with corresponding slots 1074 while the slider 970 is in the second position. Once slider 970 is in the first position, cassette 900 may be removed from cassette recess 1000 by pulling grip 972 outwardly.

Furthermore, slider 970 may be articulated from the first position to the second position when cassette 900 is not engaged with cassette recess 1000. Thus, flow stop valve 964 will operate to allow fluid to flow freely through flow stop valve 964 to outlet 914. Therefore, cassette 900 may be primed with fluid while being disengaged from cassette recess 1000 when slider 970 is in the second position (but not latched with cassette recess 1000).

Figure 9G:
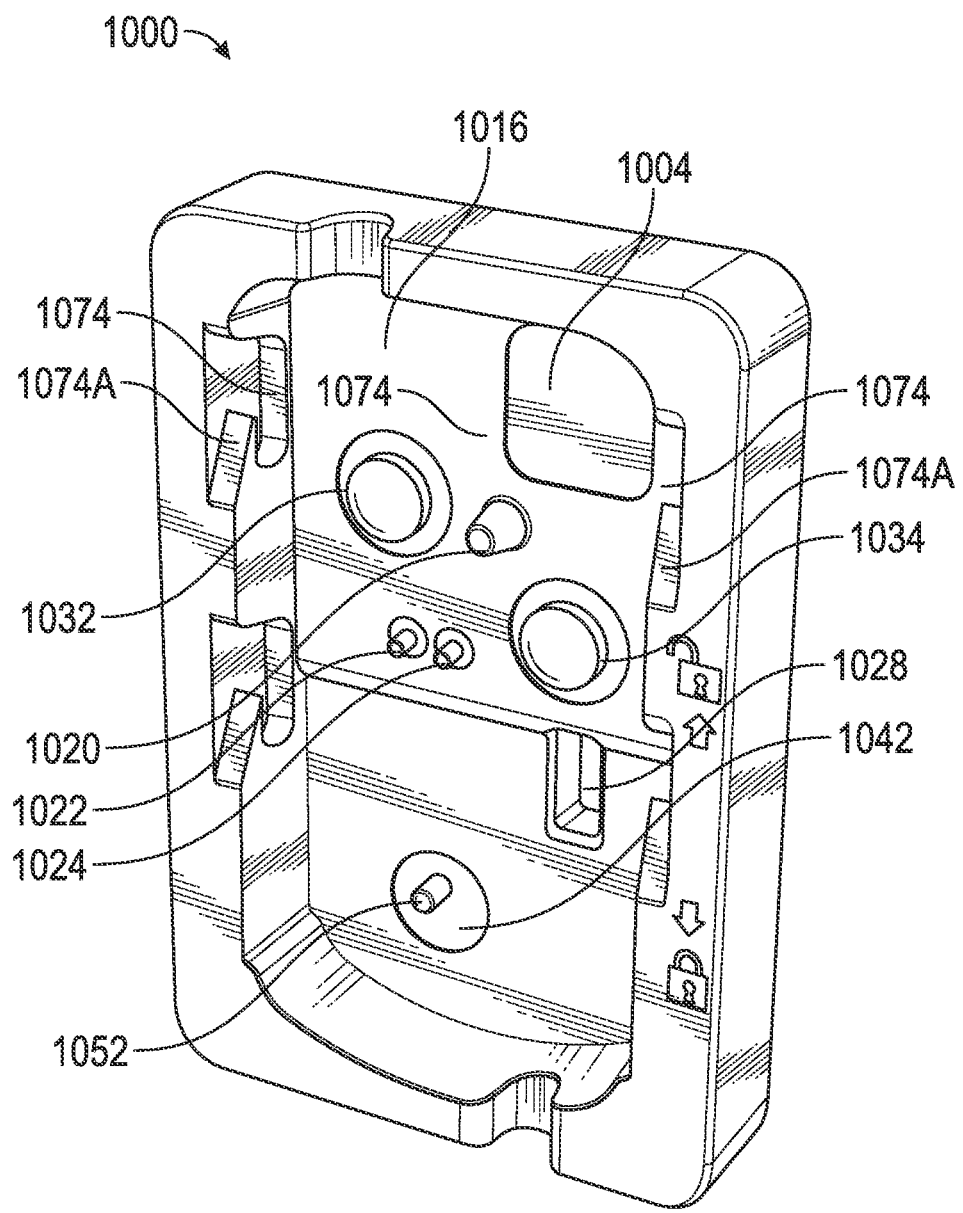
FIG. 9G illustrates a perspective view of an example of a fifth embodiment cassette recess, in accordance with aspects of the present disclosure.

It is to be understood that in other implementations, the stop valve guard feature can be a recess distal from an edge of interface-facing slider section 976, or an aperture or slit extending through interface-facing slider section 976, for example. Moreover, in some embodiments, flow stop valve and stop valve guard features may be positioned on the slider-facing side of cassette body 910. It is to be understood that various constructions of flow stop valve 964 are contemplated in the present disclosure as described herein. As illustrated in FIG. 9G, cassette recess 1000 may include interface structures operable in conjunction with infusion pump systems 10, 11. For example, pump actuator 1042 may be configured to provide a rotational force aligned with actuator-receiving portion 942 (e.g., for use with scotch-yoke pumping configurations).

Cassette recess 1000 additionally includes inlet-side valve actuator 1022 and outlet-side valve actuator 1024, in accordance with some embodiments. Inlet-side valve actuator 1022 and outlet-side valve actuator 1024 may be disposed proximate to the back surface of the cassette recess 1000, and during operation, portions of inlet-side valve actuator 1022 and outlet-side valve actuator 1024 may extend beyond the back surface (e.g., during a forward stroke of inlet-side valve actuator 1022 or outlet-side valve actuator 1024 to close inlet-side valve 922 or outlet-side valve 924, respectively).

Figure 10E:
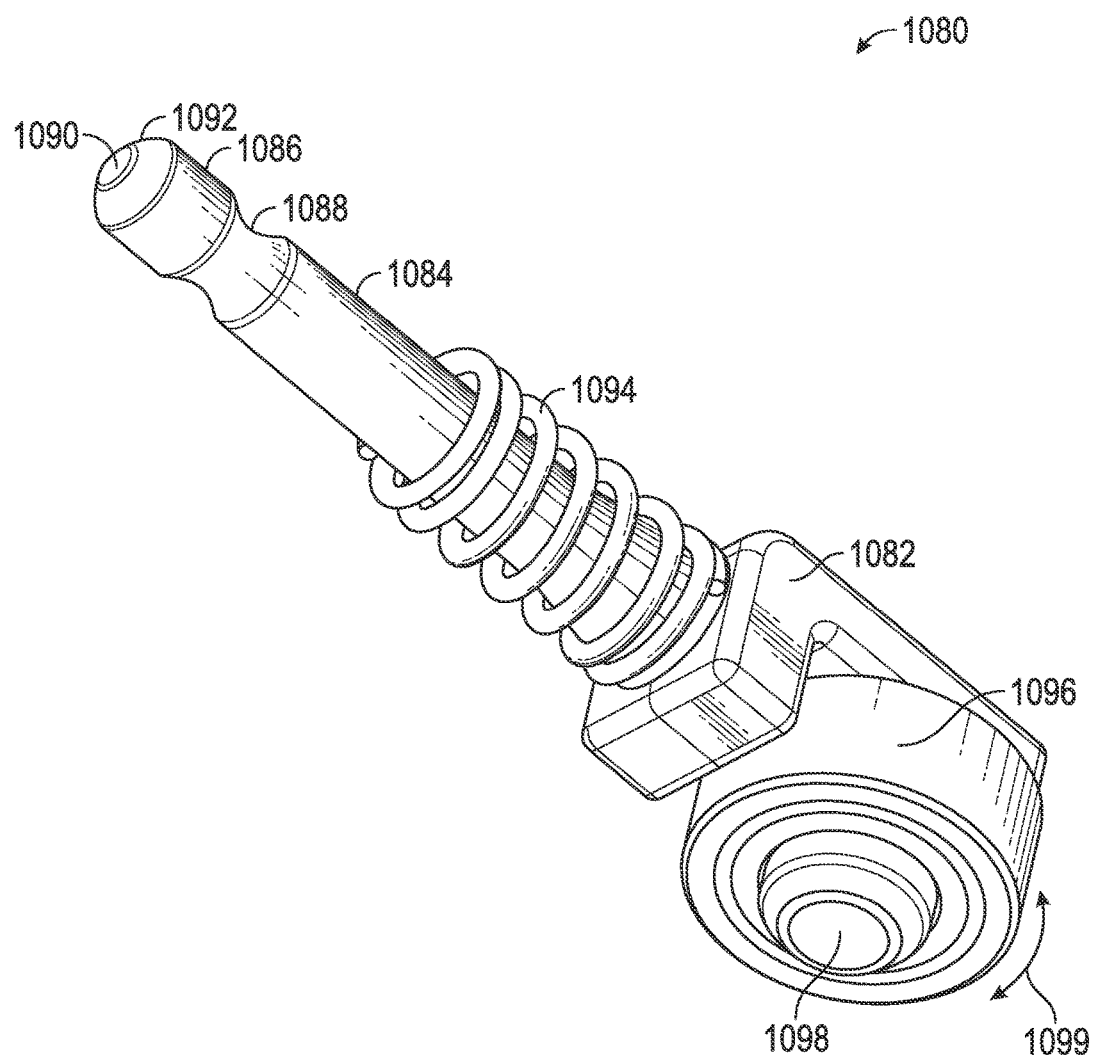
FIG. 10E illustrates an enlarged perspective view of an example of a valve actuator, in accordance with aspects of the present disclosure.

Turning now to FIG. 10E, an exemplary implementation of a valve actuator 1080 is shown. Valve actuator 1080 of FIG. 10E may, for example, be an implementation of any of valve actuators 222, 224, 422, 424, 1022 and/or 1024. In some embodiments, valve actuators 1022 and 1024 may each be one of a matched pair of valve actuators 1080. As shown in FIG. 10E, valve actuator 1080 may include a base 1082, a shaft 1084 extending from the base, and a rotatable member 1096 mounted on protrusion 1098 on the base. Rotatable member 1096 may, for example, be rotatably mounted to protrusion 1098 for rotation as indicated by arrows 1099 (e.g., in a ball-bearing assembly or other rotatable assembly). Rotatable member 1096 may be configured to rotate when contacted by a cam surface such that valve actuator 1080 moves linearly (e.g., in a direction substantially parallel to the shaft) while rotatable member 1096 is rotated. In other embodiments, member 1096 may be fixedly mounted to or integrally formed as a portion of base 1082 and may have a surface that is configured to slide along a contacting cam surface to provide the linear movement of valve actuator 1080.

As shown in FIG. 10E, a portion of shaft 1084 may be disposed within a spring 1094 mounted on the shaft and having a first end in contact with base portion 1082. An opposing end of spring 1094 may be configured to bear against an inner surface of the cassette recess 1000 when valve actuator 1080 is pushed through the back surface of the cassette recess (e.g., by contact between a cam surface and rotatable member 1096). Spring 1094 may be configured to push actuator member 1080 back into the cassette recess when a force on rotatable member 1096 is removed. In this way, forward and backward actuation of valve actuator 1080 may be provided. The forward and backward movement of a valve actuator 1080 implemented, for example, as one of valve actuators 1022 or 1024 may move a forward end 1086 of shaft 1084 against membrane 917 to push membrane 917 against a surface of cassette 900 in the fluid passageway in a corresponding valve (e.g., in one of valves 922 or 924) to close that valve.

As shown, forward portion 1086 may include a recess 1088 and a ramp portion 1092 that is tapered toward the forward surface 1090 of shaft 1084. However, it should be appreciated that the exemplary configuration shown in FIG. 10E is merely illustrative and forward end 1086 may be provided with other shapes or features as discussed herein so that forward end 1086 can provide a sufficient seal to close a valve in a fluid passageway when pressed against a membrane. In some embodiments, forward surface 1090 may be a flat surface that presses a membrane such as membrane 917 against a corresponding flat surface of cassette body 910 to close a valve. In other embodiments, forward surface 1090 or a corresponding cassette body surface may include features for enhancing the seal formed when forward portion 1086 of valve actuator 1080 is pressed against the membrane. For example, a cassette body surface in valve 922 or 924 may include a recess having a shape that corresponds to ramp portion 1092 and configured to receive the ramp portion to provide an enhanced seal (e.g., a seal capable of remaining sealed under pressures up to, for example, 40 psi) when the membrane 917 is compressed between the ramp portion of the valve actuator and the corresponding surface.

Figure 10F:
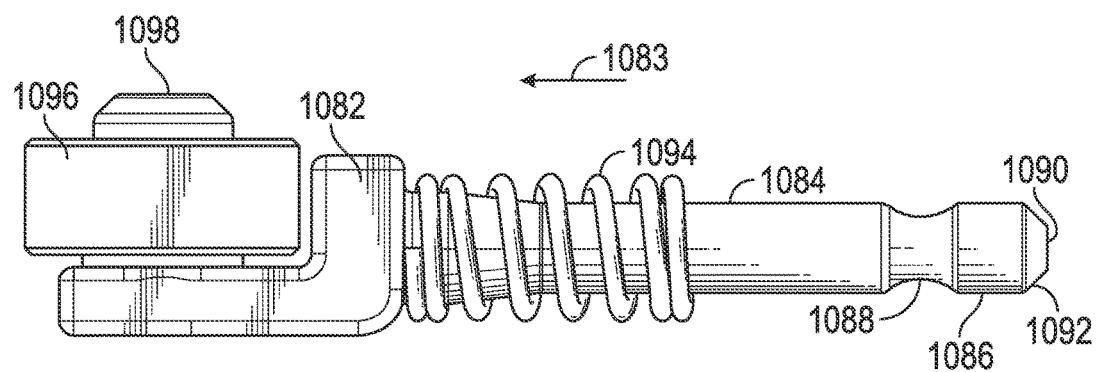
FIG. 10F illustrates an enlarged side view of an example of a valve actuator, in accordance with aspects of the present disclosure.

FIG. 10F is a side view of valve actuator 1080 according to an embodiment. As shown in FIG. 10F, rotating member 1096 may be mounted on protrusion 1098 with sufficient clearance to rotate with respect to base 1082. Valve actuator 1080 may be mounted in the cassette recess such that spring 1094 bears against an inner surface of the cassette recess and forward end 1086 protrudes through an opening in the cassette recess to engage with the membrane of the cassette. When spring 1094 is compressed (e.g., against an inner surface of the cassette recess), spring 1094 may provide a force in direction 1083 for withdrawing forward portion 1090 from the membrane to open a valve.

Figure 10G:
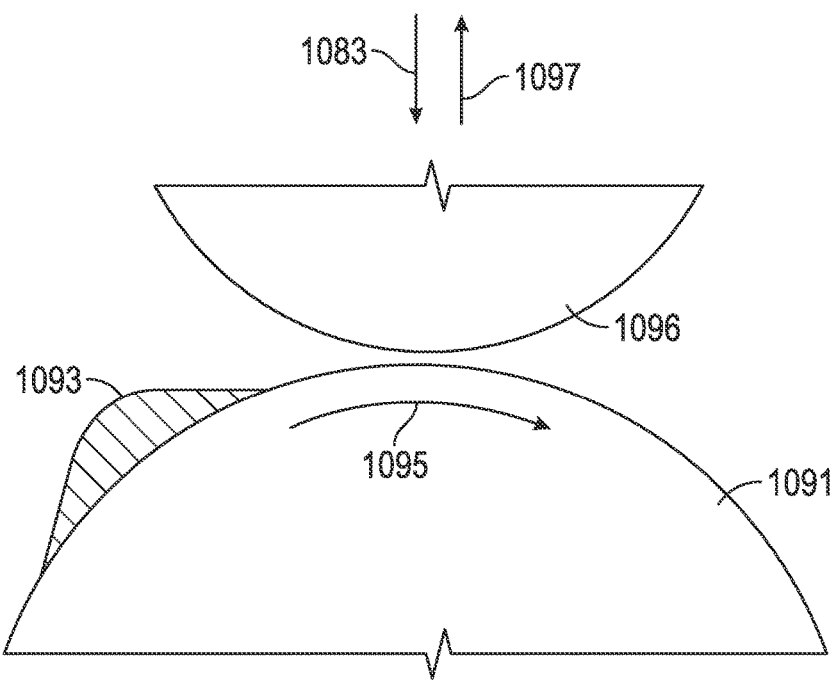
FIG. 10G illustrates diagram of an example of a valve actuator mounted in proximity to a cam for actuating the valve actuator, in accordance with aspects of the present disclosure.

FIG. 10G is an illustrative diagram of a portion of rotatable member 1096 of valve actuator 1080 showing how a cam structure such as cam 1091 may selectively bear against member 1096 to move valve actuator 1080 in direction 1097 (e.g., toward a membrane of a cassette to close a corresponding valve). In the example of FIG. 10G, cam 1091 is a rotating cam with a protrusion 1093 (e.g., attached to or integrally formed with a central rotating member) that rotates in a direction 1095 (or opposite to direction 1095) and is positioned such that the rotation causes protrusion 1093 to bear against member 1096 to push valve actuator 1080 in direction 1097. As the protrusion is further rotated away from member 1096, valve actuator 1080 may move in an opposing direction 1083 (e.g., due to the force provided by spring 1094).

It should be appreciated that the embodiment shown in FIG. 10G is merely illustrative and other mechanisms can be provided for actuating valve actuator 1080 (e.g., differently shaped cams such as non-circular or eccentric rotating members, differently shaped protrusions on a circular or other rotating member or a linear motion cam that provides a periodic or other time coordinated impulse to actuate the valve actuator). In various embodiments, a single cam structure may be rotated to operate both of a matched pair of valve actuators (e.g., an inlet-side valve actuator and an outlet-side valve actuator) by suitably positioning multiple protrusions or eccentricities on a common rotating cam structure and/or by suitably timing the rotation of a cam having a single protrusion or eccentricity to engage members 1096 of each of the matched pair of valve actuators. In other embodiments, separate cam structures may be provided and operatively coupled to a motor shaft to operate both of a matched pair of valve actuators.

In some embodiments, a scanner (or reader) may be operably coupled to infusion pump system 10, 11 (e.g., processing unit 12, 13) such that cassette identifier 902 can be scanned through window (or aperture) 1004. Additionally, an air-in-line detector may be operable to detect air in the controllable fluid path of cassette 900 via fluid pathway extension member 928, for example. Cassette recess 1000 may include various mechanical couplings and operational interfaces, such as but not limited to an inlet-side pressure sensing probe 1032 and an outlet-side pressure sensing probe recess 1034 thereby enabling measurement of in-line pressure and fault isolation to a section of the fluid pathway. For example, inlet-side pressure sensing probe 1032 may operably contact upstream pressure dome 932 through a corresponding opening of interface-facing frame portion 916. Similarly, outlet-side pressure sensing probe 934 may operably contact downstream pressure dome 934 through a corresponding opening of frame portion 916.

Figure 11A:
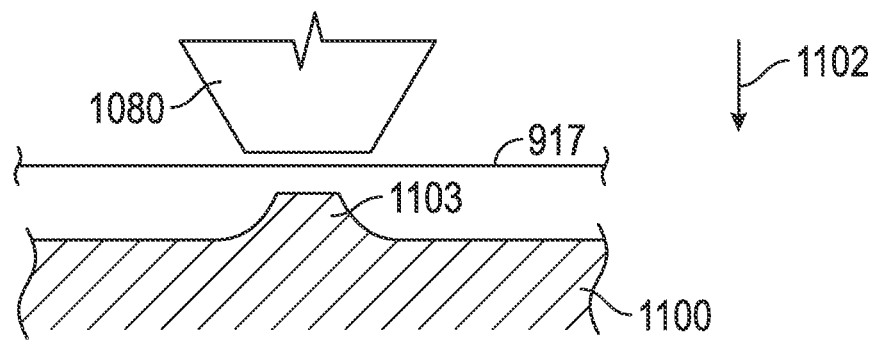
FIG. 11A illustrates an enlarged side view of an example of a valve having a valve actuator and a weir on a pump cassette surface, in accordance with aspects of the present disclosure.
Figure 11B:
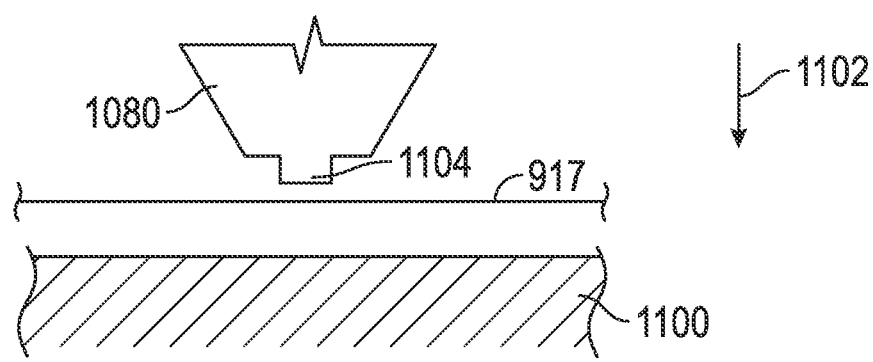
FIG. 11B illustrates an enlarged side view of an example of a valve having a valve actuator having a protrusion, in accordance with aspects of the present disclosure.
Figure 11C:
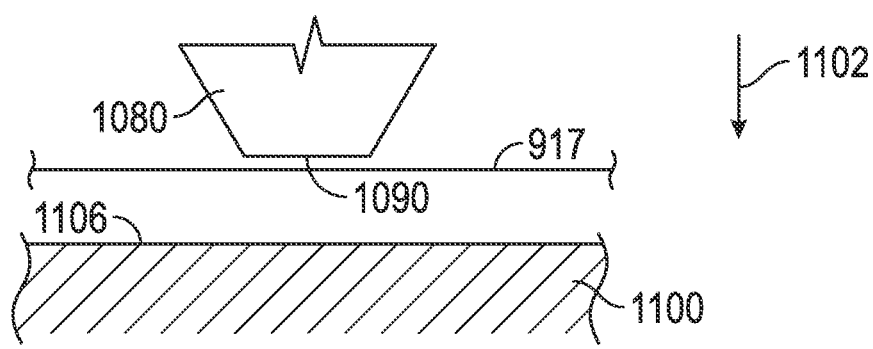
FIG. 11C illustrates an enlarged side view of an example of a valve having a valve actuator, in accordance with aspects of the present disclosure.

Turning now to FIGS. 11A-11E, various examples are shown illustrating features of valve actuator 1080 and/or a corresponding portion 1100 of cassette body 910 that may be provided for closing a valve corresponding to the valve actuator (e.g., any of valves 122, 124, 322, 324, 722, 724, 922, or 924 discussed herein). In the example of FIG. 11A, a weir-type valve is provided in which a protrusion or weir 102 is provided on portion 1100 (e.g., a portion of a cassette body structure within a fluid passageway at the location of an inlet or outlet valve). When valve actuator 1080 is moved in direction 1102 (e.g., as described above in connection with FIG. 10G), valve actuator 1080 may press a portion of membrane 917 against the weir 1102 to form a seal that closes the valve. In another embodiment, valve actuator 1080 may be provided with a protrusion 1104 on the front surface that presses the membrane 917 against a flat surface of portion 1100 to form a seal that closes the valve as shown in the example of FIG. 11B. In another embodiment, a substantially flat front surface 1090 of valve actuator 1080 may be configured to press the membrane 917 against a flat surface 1106 of portion 1100 to form a seal that closes the valve as shown in the example of FIG. 11C.

Figure 11D:
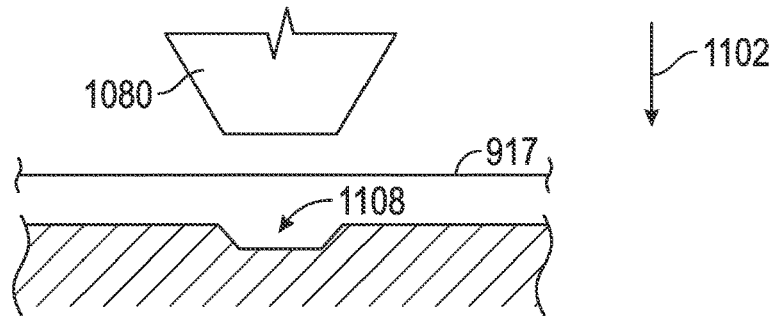
FIG. 11D illustrates an enlarged side view of an example of a valve having a valve actuator and corresponding recess on a pump cassette surface, in accordance with aspects of the present disclosure.
Figure 11E:
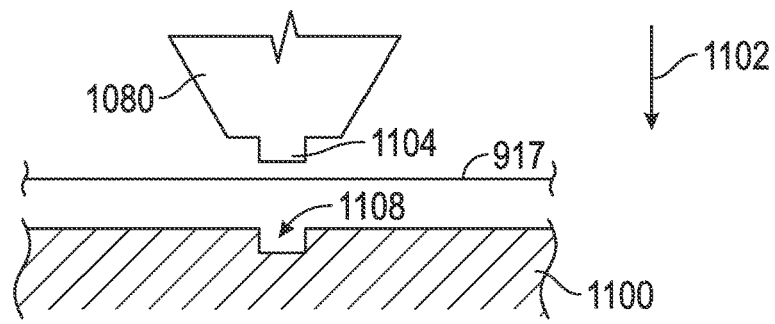
FIG. 11E illustrates an enlarged side view of an example of a valve having a valve actuator having a protrusion that interfaces with a corresponding recess on a pump cassette surface, in accordance with aspects of the present disclosure.

In yet another embodiment, valve portion 1100 may include a recess 1108 having a shape that corresponds to a ramped shape of valve actuator 1080 such that the end of valve actuator 1080 is received in recess 1108 when valve actuator 1080 is moved in direction 1102 and presses a portion of membrane 917 into recess 1108 to form a seal that closes the valve as shown in the example of FIG. 11D. In yet another embodiment, valve portion 1100 may include a recess 1108 having a shape that corresponds to a protrusion 1104 of valve actuator 1080 such that protrusion 1104 is received in recess 1108 when valve actuator 1080 is moved in direction 1102 and presses a portion of membrane 917 into recess 1108 to form a seal that closes the valve as shown in the example of FIG. 11E. In various embodiments, any or all of the features described in connection with FIGS. 11A-11E and/or other features such as ribbed surfaces of a recess or a protrusion may be included, omitted, or combined as desired to provide a seal for closing a valve of a fluid passageway formed by a cassette body and a membrane.

Figure 12:
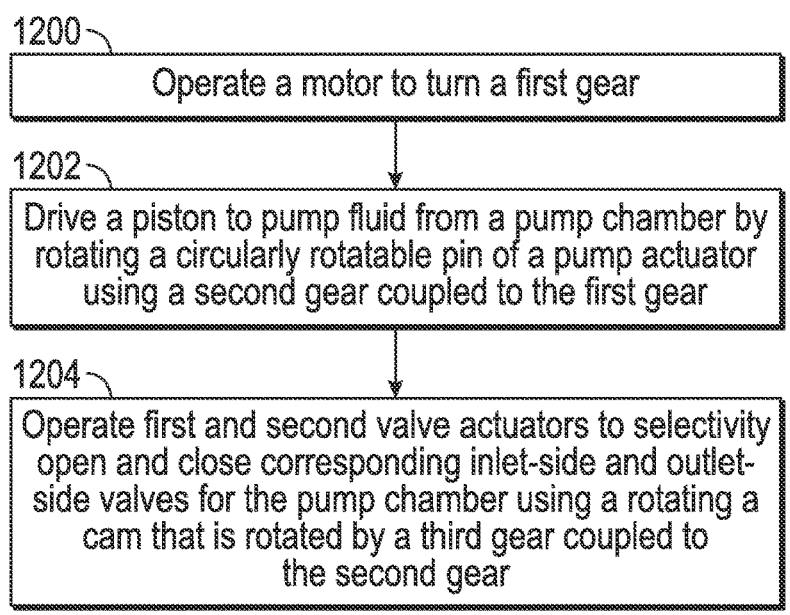
FIG. 12 illustrates a flowchart of example operations that may be performed for pumping fluids using a disposable IV pump cassette and cassette recess, in accordance with aspects of the present disclosure.

Illustrative operations that may be performed for controlling fluid flow in a fluid passageway of a pump cassette of an infusion pump system are shown in FIG. 12.

At block 1200, a motor may be operated to turn a first gear member of a gear set. In some embodiments, prior to operating the motor, a pump cassette may be provided in a cassette recess of an infusion pump system in which the motor is installed.

At block 1202, a piston may be driven to pump fluid from a pump chamber (e.g., by rotating a circularly rotatable pin of a pump actuator using, for example, a second gear member of the gear set that is coupled to the first gear). The pump chamber may be a pump chamber of the pump cassette.

At block 1204, first and second valve actuators may be operated to selectively open and close corresponding inlet-side and outlet-side valves for the pump chamber (e.g., using a rotating a cam that is rotated by a third gear member of the gear set coupled to the second gear member). In this way, one or more valves of a controllable fluid passageway in the pump cassette may be operated by actuating valve actuators that, for example, extend through a back surface of the cassette recess to contact a membrane of the pump cassette.

It is to be understood that aspects of the various embodiments disclosed herein may be intermixed and incorporated such that alternative embodiments may include one or more aspects from one or more embodiments combined in another embodiment. For example, and without limiting the scope of such combinations, alternative embodiments may include: flat face ramp portions 874a and 1074a of cassette recess 800 and 1000 with any of the other cassette recesses 200, 400, 600; flow stop valve 164 and interface-facing slider section 176 include one or more cassette-facing detents 179 of cassette 100 with any of the other cassettes 300, 700, 900;

and vertically-oriented and lockable slider grips 772 (e.g., having a flexible portion 782), 972 of cassettes 700, 900 with any of the other cassettes 100, 300.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. An infusion pump system comprising:
a processing unit; and
a cassette recess comprising at least one valve actuator configured to extend through a surface of the cassette recess to operate a valve in a fluid passageway of a cassette mounted in the cassette recess, wherein the at least one valve actuator comprises:
a base portion;
a shaft extending from the base portion through the surface; and
a spring disposed on the shaft and extending along a portion of the shaft, wherein the spring is disposed interior to the surface.

Concept 2. The infusion pump system of concept 1 or any other concept, wherein the at least one valve actuator further comprises a rotatable member disposed on the base portion and configured to be engaged by a cam structure for actuating the valve actuator in a direction substantially parallel to the shaft.

Concept 3. The infusion pump system of concept 2 or any other concept, further comprising the cam structure, wherein the cam structure is configured to periodically engage the rotatable member of the at least one valve actuator to actuate the valve actuator to operate the valve in the fluid passageway of the cassette mounted in the cassette recess.

Concept 4. The infusion pump system of concept 3 or any other concept, further comprising a rotatable pin configured to operate a piston of the cassette mounted in the cassette recess.

Concept 5. The infusion pump system of concept 4 or any other concept, wherein the at least one valve actuator further comprises a front end configured to compress a membrane of the cassette to seal the valve.

Concept 6. The infusion pump system of concept 1 or any other concept, wherein the at least one valve actuator comprises an inlet-side valve actuator and an outlet-side valve actuator, each configured to extend through the surface of the cassette recess to operate a corresponding valve in the fluid passageway in the cassette mounted in the cassette recess.

Concept 7. The infusion pump system of claim 6 or any other concept, wherein:
the fluid passageway comprises an inlet-side valve disposed between an inlet port and a pump chamber and an outlet-side valve disposed between the pump chamber and an outlet port,
the inlet-side valve actuator is configured to actuate through the surface to alternately open and close the inlet-side valve, and
the outlet-side valve actuator is configured to actuate through the back surface to alternately open and close the outlet-side valve.

Concept 8. The infusion pump system of concept 7 or any other concept, further comprising the cassette mounted in the cassette recess, the cassette comprising:
a rigid body comprising a compliant membrane, the inlet port, the outlet port, the fluid passageway defined in part by the compliant membrane and extending from the inlet port to the outlet port, wherein the inlet-side valve actuator is configured to compress a portion of the compliant membrane to close the inlet-side valve and wherein the outlet-side valve actuator is configured to compress an additional portion of the compliant membrane to close the outlet-side valve.

Concept 9. The infusion pump system of concept 1 or any other concept, wherein the at least one valve actuator comprises a forward end having at least one feature configured to engage with a corresponding feature of the cassette to provide a seal to close the valve.

Concept 10. A valve actuator, comprising:
a base portion;
a shaft extending from the base portion;
a spring disposed on the shaft and extending along a portion of the shaft; and
a rotatable member disposed on the base portion and configured to be engaged by a cam structure for actuating the valve actuator in a direction substantially parallel to the shaft.

Concept 11. The valve actuator of concept 10 or any other concept, wherein the base portion includes a protrusion that extends in a direction substantially perpendicular to the shaft and wherein the rotatable member is rotatably mounted on the protrusion.

Concept 12. The valve actuator of claim 10 or any other concept, wherein the shaft comprises a forward end having a ramp portion configured to engage a corresponding recess in an external structure.

Concept 13. The valve actuator of concept 10 or any other concept or any other concept, wherein the shaft comprises a forward end having a protrusion configured to engage a corresponding recess in an external structure.

Concept 14. The valve actuator of concept 10 or any other concept, wherein the shaft comprises a forward end having a recess configured to engage a corresponding protrusion in an external structure.

Concept 15. The valve actuator of concept 10 or any other concept, wherein the spring has a first end configured to engage the base portion and a second end configured to engage an interior surface of a cassette recess of an infusion pump system and wherein the shaft is configured to extend through the interior surface to open and close a valve in a fluid passageway in a pump cassette mounted in the cassette recess.

Concept 16. A method of operating an infusion pump system, comprising:
providing a pump cassette in a cassette recess of the infusion pump system; and
operating a valve of a controllable fluid passageway in the pump cassette by actuating a valve actuator that extends through a back surface of the cassette recess to contact a membrane of the pump cassette, wherein the valve actuator comprises:
a base portion;
a shaft extending from the base portion through the back surface; and
a spring disposed on the shaft and extending along a portion of the shaft, wherein the spring is disposed interior to the back surface.

Concept 17. The method of concept 16 or any other concept, wherein operating the valve comprises closing the valve by engaging a rotatable member of the actuator with a cam structure that causes a forward end of the shaft to move in a first direction through the back surface to compress a portion of the membrane of the cassette.

Concept 18. The method of concept 17 or any other concept, wherein operating the valve further comprises opening the valve by disengaging the cam structure from the rotatable member to allow the spring to move the shaft in a second opposite direction.

Concept 19. The method of concept 18 or any other concept, wherein the engaging and disengaging of the cam structure comprise rotating the cam structure by operating a motor that is operatively coupled to the cam structure by a gear set.

Concept 20. The method of concept 19 or any other concept, wherein the gear set is operatively coupled to a pump actuator and wherein operating the motor further comprises operating the pump actuator to drive a piston that, in cooperation with the valve actuator controllably pumps fluid through the controllable fluid passageway.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An infusion pump system comprising: a cassette recess comprising at least one valve actuator configured to extend through a surface of the cassette recess to operate a valve in a fluid passageway of a cassette mounted in the cassette recess, wherein the at least one valve actuator comprises: a base portion; a shaft extending from the base portion through the surface; a spring disposed on the shaft and extending along a portion of the shaft, wherein the spring is disposed interior to the surface; and a rotatable member disposed on the base portion; and a cam structure configured to periodically bear against the rotatable member of the at least one valve actuator to actuate the at least one valve actuator in a direction substantially parallel to the shaft, wherein the cam structure comprises a rotating cam having a protrusion or eccentricity that is configured to slide against the rotatable member to cause linear movement of the at least one valve actuator in the direction substantially parallel to the shaft.

2. The infusion pump system of claim 1, wherein the shaft comprises a forward end having a ramp portion configured to engage a recess in a surface of the cassette.

3. The infusion pump system of claim 1, wherein the spring has a first end configured to engage the base portion and a second end configured to engage an interior surface of the cassette recess.

4. The infusion pump system of claim 1, further comprising a rotatable pin that is mechanically separate from the at least one valve actuator and that is configured to operate a piston of the cassette mounted in the cassette recess.

5. The infusion pump system of claim 4, wherein the at least one valve actuator further comprises a front end configured to compress a membrane of the cassette to seal the valve.

6. The infusion pump system of claim 1, wherein the at least one valve actuator comprises an inlet-side valve actuator configured to extend through the surface of the cassette recess to operate the valve in the fluid passageway in the cassette mounted in the cassette recess and an outlet-side valve actuator configured to extend through the surface of the cassette recess to operate an additional valve in the fluid passageway in the cassette mounted in the cassette recess, the valve being an inlet-side valve and the additional valve being an outlet-side valve.

7. The infusion pump system of claim 6, wherein the cam structure comprises a single rotating cam configured operate both of the inlet-side valve actuator and the outlet-side valve actuator.

8. The infusion pump system of claim 6, further comprising the cassette and the fluid passageway, the inlet-side valve, and the outlet-side valve, wherein:
the fluid passageway comprises the inlet-side valve disposed between an inlet port and a pump chamber and the outlet-side valve disposed between the pump chamber and an outlet port,
the inlet-side valve actuator is configured to actuate through the surface to alternately open and close the inlet-side valve, and
the outlet-side valve actuator is configured to actuate through the surface to alternately open and close the outlet-side valve.

9. The infusion pump system of claim 8, the cassette comprising:
a rigid body comprising a compliant membrane, the inlet port, the outlet port, the fluid passageway defined in part by the compliant membrane and extending from the inlet port to the outlet port, wherein the inlet-side valve actuator is configured to compress a portion of the compliant membrane to close the inlet-side valve and wherein the outlet-side valve actuator is configured to compress an additional portion of the compliant membrane to close the outlet-side valve.

10. A system for actuating a valve, the system comprising: a base portion; a shaft extending from the base portion and configured to extend through a surface of a cassette recess of an infusion pump system to operate a valve in a fluid passageway of a cassette mounted in the cassette recess; a spring disposed on the shaft and extending along a portion of the shaft, wherein the spring is configured to be disposed interior to the surface; a rotatable member disposed on the base portion; and a cam structure configured to periodically bear against the rotatable member to cause movement of the shaft in a direction substantially parallel to the shaft, wherein the cam structure comprises a rotating cam having a protrusion or eccentricity that is configured to slide against the rotatable member to cause linear movement of the shaft in the direction substantially parallel to the shaft.

11. The system of claim 10, wherein the shaft comprises a forward end having a ramp portion configured to engage a corresponding recess in an external structure.

12. The system of claim 10, wherein the shaft comprises a forward end having a protrusion configured to engage a corresponding recess in an external structure.

13. The system of claim 10, wherein the shaft comprises a forward end having a recess configured to engage a corresponding protrusion in an external structure.

14. The system of claim 10, wherein the spring has a first end configured to engage the base portion and a second end configured to engage an interior surface of the cassette recess and wherein the shaft is configured to extend through the interior surface to open and close the valve.

15. A method of operating an infusion pump system, comprising: providing a pump cassette in a cassette recess of the infusion pump system; and operating a valve of a controllable fluid passageway in the pump cassette by actuating a valve actuator that extends through a back surface of the cassette recess to contact a membrane of the pump cassette, wherein the valve actuator comprises: a base portion; a shaft extending from the base portion through the back surface; a spring disposed on the shaft and extending along a portion of the shaft, wherein the spring is disposed interior to the back surface; and a rotatable member disposed on the base portion, wherein operating the valve comprises periodically bearing against the rotatable member of the valve actuator with a cam structure to actuate the valve actuator in a direction substantially parallel to the shaft, wherein periodically bearing against the rotatable member comprises sliding against the rotatable member with a protrusion or eccentricity of a rotating cam of the cam structure to cause linear movement of the valve actuator in the direction substantially parallel to the shaft.

16. The method of claim 15, wherein operating the valve comprises closing the valve by engaging the rotatable member of the valve actuator with the cam structure to cause a forward end of the shaft to move in a first direction through the back surface to compress a portion of the membrane of the cassette.

17. The method of claim 16, wherein operating the valve further comprises opening the valve by disengaging the cam structure from the rotatable member to allow the spring to move the shaft in a second direction opposite to the first direction.

18. The method of claim 17, wherein the engaging and disengaging of the cam structure comprise rotating the cam structure by operating a motor that is operatively coupled to the cam structure by a gear set.

19. The method of claim 18, wherein the gear set is operatively coupled to a pump actuator and wherein operating the motor further comprises operating the pump actuator to drive a piston that, in cooperation with the valve actuator controllably pumps fluid through the controllable fluid passageway.

* * * * *